United States Patent
Asami et al.

(10) Patent No.: US 9,200,051 B2
(45) Date of Patent: Dec. 1, 2015

(54) PEPTIDE COMPOUND

(71) Applicant: TAKEDA PHARMACEUTICAL COMPANY LIMITED, Osaka (JP)

(72) Inventors: Taiji Asami, Kanagawa (JP); Ayumu Niida, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/287,514

(22) Filed: May 27, 2014

(65) Prior Publication Data
US 2014/0357552 A1 Dec. 4, 2014

(30) Foreign Application Priority Data
May 28, 2013 (JP) ................................. 2013-111893

(51) Int. Cl.
C07K 14/605 (2006.01)
(52) U.S. Cl.
CPC .................................... C07K 14/605 (2013.01)
(58) Field of Classification Search
None
See application file for complete search history.

(56) References Cited

U.S. PATENT DOCUMENTS

2003/0157107 A1  8/2003  Miyawaki et al.

FOREIGN PATENT DOCUMENTS

| WO | 98/19698 | 5/1998 |
|---|---|---|
| WO | 98/20895 | 5/1998 |
| WO | 99/47161 | 9/1999 |
| WO | 00/07617 | 2/2000 |
| WO | 01/87341 | 11/2001 |
| WO | 2004/005342 | 1/2004 |
| WO | 2006/086769 | 8/2006 |
| WO | 2006/136374 | 12/2006 |
| WO | 2008/008357 | 1/2008 |
| WO | 2008/021560 | 2/2008 |
| WO | 2008/033888 | 3/2008 |
| WO | 2009/067268 | 5/2009 |
| WO | 2010/011439 | 1/2010 |
| WO | 2010/068735 | 6/2010 |
| WO | 2010/148089 | 12/2010 |
| WO | 2011/119657 | 9/2011 |
| WO | 2012/088379 | 6/2012 |
| WO | 2012/138941 | 10/2012 |
| WO | 2012/167744 | 12/2012 |
| WO | 2013/003449 | 1/2013 |
| WO | 2013/164483 | 11/2013 |
| WO | 2013/192129 | 12/2013 |
| WO | 2013/192130 | 12/2013 |
| WO | 2014/096179 | 6/2014 |

OTHER PUBLICATIONS

Prophylaxis. (n.d.). Dictionary.com Unabridged. Retrieved May 15, 2015, from Dictionary.com website: http://dictionary.reference.com/browse/prophylaxis; pp. 1/3.*
Huang et al., "Resolving the Conundrum of Islet Transplantation by Linking Metabolic Dysregulation, Inflammation, and Immune Regulation", Endocrine Reviews, 2008; pp. 603-630.*
Hancock, "Preventing and managing diabetes: an exemplar for NCDs", C3 Collaborating for Health, www.c3health.org, 2012, pp. 1-8.*
eMedicine Health, Gestational Diabetes—Prevention: Healthwise Medical Information on eMedicineHealth; http://www.emedicinehealth.com/script/main/art.asp?articlekey=128918&pf=3&page=9; pp. 1-2; obtained May 13, 2015.*
Choquet et al., "Genetics of Obesity: What have we Learned?", Current Genomics, 2011, pp. 169-179.*
He et al., " Reversal of Obesity and Insulin Resistance by a Non-Peptidic Glucagon-Like Peptide-1 Receptor Agonist in Diet-Induced Obese Mice" PLOS One, 2010, pp. 1-15.*
Finan et al., "A rationally designed monomeric peptide triagonist corrects obesity and diabetes in rodents", Nature Medicine, 2015; pp. 27-39.*
International Search Report issued Sep. 22, 2014 in International (PCT) Application No. PCT/JP2014/002772.
Runge et al., "Differential Structural Properties of GLP-1 and Exendin-4 Determine Their Relative Affinity for the GLP-1 Receptor N-Terminal Extracellular Domain", Biochemistry, vol. 46, Apr. 2007, pp. 5830-5840.
Al-Sabah et al., "A model for receptor-peptide binding at the glucagon-like peptide-1 (GLP-1) receptor through the analysis of truncated ligands and receptors", British Journal of Pharmacology, vol. 140, Aug. 2003, pp. 339-346.
Gault et al., "Administration of an acylated GLP-1 and GIP preparation provides added beneficial glucose-lowering and insulinotropic actions over single incretins in mice with Type 2 diabetes and obesity", Clinical Science, vol. 121, 2011, pp. 107-117.

* cited by examiner

Primary Examiner — Karlheinz R Skowronek
Assistant Examiner — Lianko Garyu
(74) Attorney, Agent, or Firm — Wenderoth, Lind & Ponack, L.L.P.

(57) ABSTRACT

The present invention provides a novel peptide compound having an activating action on GLP-1 receptors and GIP receptors and use of the peptide compound as a medicament. Specifically, a peptide containing a partial sequence represented by the formula (I) or a salt thereof and a medicament comprising the same are provided. $P^1$-Tyr-Aib-Glu-Gly-Thr-αMePhe-Thr-Ser-Asp-Tyr-A11-A12-A13-Leu-Asp-A16-A17-Ala-Gln-A20-Glu-Phe-Val-Lys-Trp-Leu-Leu-Lys-A29 SEQ ID NO: 1 (I)
wherein each symbol is as defined herein.

4 Claims, No Drawings

PEPTIDE COMPOUND

TECHNICAL FIELD

The present invention relates to a novel peptide compound having an activating action on GLP-1 receptors and GIP receptors and use of the peptide compound as a medicament.

BACKGROUND OF THE INVENTION

Both glucagon-like peptide-1 (GLP-1) and glucose-dependent insulinotropic polypeptide (GIP) are peptides called incretin. GLP-1 and GIP are secreted from small intestinal L cells and K cells, respectively.

GLP-1 acts via GLP-1 receptors and is known to have a glucose-dependent insulinotropic action and a feeding suppressive action. On the other hand, GIP is known to have a glucose-dependent insulinotropic action via GIP receptors, though its influence on feeding is not clear.

The co-administration of a GLP-1 receptor agonist liraglutide and a GIP receptor agonist N-Ac-GIP has been reported to more promote a glucose tolerance-improving action and a body weight-lowering action than the administration of liraglutide alone (Non Patent Literature 1). Also, a GLP-1 receptor/GIP receptor coagonist peptide has been reported to show a stronger hypoglycemic action and body weight-lowering action than those of a GLP-1 receptor agonist alone (Patent Literature 1).

Attempts have also been made to search for peptides having GLP-1 receptor/GIP receptor coagonist or glucagon/GLP-1 receptor/GIP receptor triagonist activity and develop these peptides as anti-obesity drugs or therapeutic drugs for diabetes, on the basis of the structure of natural glucagon, GIP, or GLP-1 (Patent Literatures 1 to 8). None of the literatures, however, disclose the peptide compound of the present invention.

CITATION LIST

Patent Literature

[Patent Literature 1] WO2010/011439
[Patent Literature 2] WO2010/148089
[Patent Literature 3] WO2011/119657
[Patent Literature 4] WO2012/088379
[Patent Literature 5] WO2012/167744
[Patent Literature 6] WO2013/164483
[Patent Literature 7] WO2013/192129
[Patent Literature 8] WO2013/192130

Non Patent Literature

[Non Patent Literature 1] Clinical Science 121, 107-117 (2011)

SUMMARY OF INVENTION

Technical Problem

The present invention aims to provide a novel peptide compound having high GLP-1 receptor/GIP receptor coagonist activity, and useful as an agent for the prophylaxis or treatment of obesity and the like.

Solution to Problem

The present inventors have conducted intensive studies about a novel peptide compound having superior GLP-1 receptor/GIP receptor coagonist activity, and useful as an agent for the prophylaxis or treatment of obesity and the like, and consequently found that a peptide compound containing a partial sequence represented by the formula (I) shown below, and the like have superior GLP-1 receptor/GIP receptor coagonist activity, which resulted in the completion of the present invention.

Accordingly, the present invention relates to

[1] a peptide comprising a partial sequence represented by the formula (I):

(SEQ ID NO: 1)
$P^1$-Tyr-Aib-Glu-Gly-Thr-αMePhe-Thr-Ser-Asp-Tyr-A11-A12-A13-Leu-Asp-A16-A17-Ala-Gln-A20-Glu-Phe-Val-Lys-Trp-Leu-Leu-Lys-A29 wherein
$P^1$ is a group represented by the formula:
—$R^{41}$,
—CO—$R^{41}$,
—CO—$OR^{41}$,
—CO—$COR^{41}$,
—SO—$R^{41}$,
—$SO_2$—$R^{41}$,
—$SO_2$—$OR^{41}$,
—CO—$NR^{42}R^{43}$,
—$SO_2$—$NR^{42}R^{43}$, or
—C(=$NR^{41}$)—$NR^{42}R^{43}$
wherein $R^{41}$, $R^{42}$ and $R^{43}$ are each independently a hydrogen atom, an optionally substituted hydrocarbon group, or an optionally substituted heterocyclic group;
A11 is Aib or Ala;
A12 is Ala, Ile, Lys, Phe or Pya(4);
A13 is Aib, Cha, Leu, αMePhe or α-MeTyr;
A16 is Lys or Ser;
A17 is Gln or Ile;
A20 is Ala or Ser; and
A29 is Gln or Gly,
or a salt thereof (hereinafter sometimes to be abbreviated as compound (I));

[2]
The peptide of the above-mentioned [1] or a salt thereof, wherein $P^1$ is a hydrogen atom;

[3]
The peptide of the above-mentioned [1] or a salt thereof, wherein A11 is Aib;

[4]
The peptide of the above-mentioned [1] or a salt thereof, wherein A12 is Ile;

[5]
The peptide of the above-mentioned [1] or a salt thereof, wherein A13 is Aib;

[6]
The peptide of the above-mentioned [1] or a salt thereof, wherein A16 is Lys;

[7]
The peptide of the above-mentioned [1] or a salt thereof, wherein A17 is Gln;

[8]
The peptide of the above-mentioned [1] or a salt thereof, wherein A20 is Ala;

[9]
The peptide of the above-mentioned [1] or a salt thereof, wherein A29 is Gly;

[10]
The peptide of the above-mentioned [1] or a salt thereof, having an amino acid sequence represented by Gly-Pro-Ser-Ser-Gly-Ala-Pro-Pro-Pro-Ser-Lys-(SEQ ID NO: 2) on the C-terminal side of A29;

[11]
The peptide of the above-mentioned [1] or a salt thereof, wherein
$P^1$ is a hydrogen atom;
A11 is Aib;
A12 is Ile;
A13 is Aib;
A16 is Lys;
A17 is Gln;
A20 is Ala;
A29 is Gly; and
the peptide having an amino acid sequence represented by Gly-Pro-Ser-Ser-Gly-Ala-Pro-Pro-Pro-Ser-Lys-(SEQ ID NO: 2) on the C-terminal side of A29;

[12]
H-Tyr-Aib-Glu-Gly-Thr-αMePhe-Thr-Ser-Asp-Tyr-Aib-Lys-Tyr-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 36) or a salt thereof;

[13]
H-Tyr-Aib-Glu-Gly-Thr-αMePhe-Thr-Ser-Asp-Tyr-Aib-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 14) or a salt thereof;

[14]
H-Tyr-Aib-Glu-Gly-Thr-αMePhe-Thr-Ser-Asp-Tyr-Aib-Lys-Tyr-Leu-Asp-Lys-Gln-Ala-Gln-Gln-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 37) or a salt thereof;

[15]
H-Tyr-Aib-Glu-Gly-Thr-αMePhe-Thr-Ser-Asp-Tyr-Aib-Lys-Tyr-Leu-Asp-Lys-Gln-Ala-Gln-Gln-Glu-Phe-Val-Lys-Trp-Leu-Leu-Lys-Gly-Gly-Pro-Ser-Ser-Gly-Ala-Pro-Pro-Pro-Ser-NH$_2$ (SEQ ID NO: 38) or a salt thereof;

[16]
a medicament comprising the peptide of the above-mentioned [1] or a salt thereof;

[17]
the medicament of the above-mentioned [16], which is an activator of a GLP-1 receptor and a GIP receptor;

[18]
the medicament of the above-mentioned [16], which is an agent for the prophylaxis or treatment of obesity or diabetes;

[19]
A method for the prophylaxis or treatment of obesity or diabetes in a mammal, comprising administering an effective amount of the peptide of the above-mentioned
[1] or a salt thereof to the mammal;

[20]
A method for activating a GLP-1 receptor and a GIP receptor in a mammal, comprising administering an effective amount of the peptide of the above-mentioned [1] or a salt thereof to the mammal;

[21]
Use of the peptide of the above-mentioned [1] or a salt thereof for the manufacture of an agent for the prophylaxis or treatment of obesity or diabetes;

[22]
The peptide of the above-mentioned [1] or a salt thereof for use in the prophylaxis or treatment of obesity or diabetes.

Advantageous Effects of Invention

Compound (I) has superior GLP-1 receptor/GIP receptor coagonist activity, and shows significant feeding suppressive and body weight-lowering effects in vivo. In addition, compound (I) has a low risk of hyperglycemic action, and is also useful in the treatment of obesity associated with diabetes and the like, because of its low glucagon receptor agonist activity. Moreover, compound (I) is excellent in solubility, and also has the advantage that the compound can be easily formulated as a medicament.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A. [substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,

(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and
9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkyl-sulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

The definition of each symbol in the formula (I) is described in detail in the following.

$P^1$ is a group represented by the formula:
—$R^{41}$
—CO—$R^{41}$,
—CO—$OR^{41}$, —CO—COR$^{41}$,
—SO_R$^{41}$,
—SO$_2$—R$^{41}$,
—SO$_2$—OR$^{41}$,
—CO—NR$^{42}$R$^{43}$,
—SO$_2$—NR$^{42}$R$^{43}$, or
—C(=NR$^{41}$)—NR$^{42}$R$^{43}$
wherein R$^{41}$, R$^{42}$ and R$^{43}$ are each independently a hydrogen atom, an optionally substituted hydrocarbon group, or optionally substituted heterocyclic group.

P$^1$ is preferably a hydrogen atom.
A11 is Aib or Ala.
A11 is preferably Aib.
A12 is Ala, Ile, Lys, Phe or Pya(4).
A12 is preferably Ile.
In an alternative embodiment, A12 is preferably Lys.
A13 is Aib, Cha, Leu, αMePhe or αMeTyr.
A13 is preferably Aib.
A16 is Lys or Ser.
A16 is preferably Lys.
A17 is Gln or Ile.
A17 is preferably Gln.
A20 is Ala or Ser.
A20 is preferably Ala.
A29 is Gln or Gly.
A29 is preferably Gly.

Compound (I) may have an additional peptide sequence on the C-terminal side (C-terminal sequence) of A29 in the partial sequence represented by the formula (I).

Here, the length of the C-terminal sequence is not particularly limited and is preferably 1 to 11 amino acid residues, more preferably 6 to 11 amino acid residues.

Examples of the C-terminal sequence can include (i) an amino acid sequence represented by Gly-Pro-Ser-Ser-Gly-Ala-Pro-Pro-Pro-Ser-Lys (SEQ ID NO: 2), (ii) an amino acid sequence derived from the sequence of the above-mentioned (i) by the deletion, substitution (preferably, conservative substitution), or addition of 1 to 11, preferably 1 to 5 amino acids, and (iii) a partial sequence comprising at least 1 (consecutive) amino acid residue, preferably 6 consecutive amino acid residues, from the N-terminal side of the sequence of the above-mentioned (i) or (ii).

As the C-terminal sequence, (1)
Gly-, (2)
Gly-Pro-, (3)
Gly-Pro-Ser-, (4)
(SEQ ID NO: 3)
Gly-Pro-Ser-Ser-, (5)
(SEQ ID NO: 4)
Gly-Pro-Ser-Ser-Gly-, (6)
(SEQ ID NO: 5)
Gly-Pro-Ser-Ser-Gly-Ala-, (7)
(SEQ ID NO: 6)
Gly-Pro-Ser-Ser-Gly-Ala-Pro-, (8)
(SEQ ID NO: 7)
Gly-Pro-Ser-Ser-Gly-Ala-Pro-Pro-, (9)
(SEQ ID NO: 8)
Gly-Pro-Ser-Ser-Gly-Ala-Pro-Pro-Pro-,

(10)
(SEQ ID NO: 9)
Gly-Pro-Ser-Ser-Gly-Ala-Pro-Pro-Pro-Ser-,

(11)
(SEQ ID NO: 2)
Gly-Pro-Ser-Ser-Gly-Ala-Pro-Pro-Pro-Ser-Lys-, or the like is specifically used.

The C-terminal sequence is preferably Gly-Pro-Ser-Ser-Gly-Ala-Pro-Pro-Pro-Ser-(SEQ ID NO: 9) or Gly-Pro-Ser-Ser-Gly-Ala-Pro-Pro-Pro-Ser-Lys-(SEQ ID NO: 2).

The C-terminal sequence is particularly preferably Gly-Pro-Ser-Ser-Gly-Ala-Pro-Pro-Pro-Ser-Lys-(SEQ ID NO: 2.

Compound (I) having the above-mentioned C-terminal sequence has superior solubility.

Also, compound (I) having the above-mentioned C-terminal sequence has high GLP-1 receptor and GIP receptor activating action in vivo.

Preferable examples of compound (I) include the following peptide or a salt thereof.

[Compound A]
Compound (I) wherein
P$^1$ is a hydrogen atom;
A11 is Aib;
A12 is Ile;
A13 is Aib;
A16 is Lys;
A17 is Gln;
A20 is Ala;
A29 is Gly; and
the peptide having an amino acid sequence represented by Gly-Pro-Ser-Ser-Gly-Ala-Pro-Pro-Pro-Ser-Lys-(SEQ ID NO: 2) on the C-terminal side of A29.

Compound (I) can be produced according to a peptide synthesis method known per se. The peptide synthesis method may be any of, for example, a solid phase synthesis process and a liquid phase synthesis process. That is, the object peptide can be produced by repeating condensation of a partial peptide or amino acid capable of constituting compound (I) and the remaining portion (which may be constituted by two or more amino acids) according to a desired sequence. When a product having the desirable sequence has a protecting group, the object peptide can be produced by eliminating a protecting group. Examples of the condensing method and eliminating method of a protecting group to be known include methods described in the following (1)-(5).

(1) M. Bodanszky and M. A. Ondetti: Peptide Synthesis, Interscience Publishers, New York (1966)
(2) Schroeder and Luebke: The Peptide, Academic Press, New York (1965)
(3) Nobuo Izumiya, et al.: Peptide Gosei-no-Kiso to Jikken (Basics and experiments of peptide synthesis), published by Maruzen Co. (1975)
(4) Haruaki Yajima and Shunpei Sakakibara: Seikagaku Jikken Koza (Biochemical Experiment) 1, Tanpakushitsu no Kagaku (Chemistry of Proteins) IV, 205 (1977)
(5) Haruaki Yajima, ed.: Zoku Iyakuhin no Kaihatsu (A sequel to Development of Pharmaceuticals), Vol. 14, Peptide Synthesis, published by Hirokawa Shoten After the reaction, compound (I) can be purified and isolated using conventional methods of purification, such as solvent extraction, distillation, column chromatography, liquid chromatography, recrystallization, etc., in combination thereof. When the peptide obtained by the above-mentioned method is in a free form, it can be converted to a suitable salt by a known method; conversely, when the peptide is obtained in the form of a salt, the salt can be converted to a free form or other salt by a known method.

The starting compound may also be a salt. Examples of such salt include those exemplified as salts of compound (I) mentioned bellow.

For condensation of protected amino acid or peptide, various activation reagents usable for peptide synthesis can be used, which are particularly preferably trisphosphonium salts, tetramethyluronium salts, carbodiimides and the like. Examples of the trisphosphonium salt include benzotriazol-1-yloxytris(pyrrolizino)phosphoniumhexafluorophosphate (PyBOP), bromotris(pyrrolizino)phosphoniumhexafluorophosphate (PyBroP), 7-azabenzotriazol-1-yloxytris(pyrrolizino)phosphoniumhexafluorophosphate (PyAOP), examples of the tetramethyluronium salt include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluroniumtetrafluoroborate (TBTU), 2-(5-norbornane-2,3-dicarboxyimide)-1,1,3,3-tetramethyluroniumtetrafluoroborate (TNTU), 0-(N-succimidyl)-1,1,3,3-tetramethyluroniumtetrafluoroborate (TSTU), and examples of the carbodiimide include DCC, N,N diisopropylcarbodiimide (DIPCDI), N-ethyl-N'-(3-dimethylaminopropyl)carbodiimide hydrochloride (EDCI•HCl) and the like. For condensation using these, addition of a racemization inhibitor (e.g., HONB, HOBt, HOAt, HOOBt etc.) is preferable. A solvent to be used for the condensation can be appropriately selected from those known to be usable for peptide condensation reaction. For example, acid amides such as anhydrous or water-containing N,N-dimethylformamide, N,N-dimethylacetamide, N-methylpyrrolidone and the like, halogenated hydrocarbons such as methylene chloride, chloroform and the like, alcohols such as trifluoroethanol, phenol and the like, sulfoxides such as dimethylsulfoxide and the like, tertiary amines such as pyridine and the like, ethers such as dioxane, tetrahydrofuran and the like, nitriles such as acetonitrile, propionitrile and the like, esters such as methyl acetate, ethyl acetate and the like, an appropriate mixture of these and the like can be used. Reaction temperature is appropriately selected from the range known to be usable for peptide binding reactions, and is normally selected from the range of about −20° C. to 50° C. An activated amino acid derivative is normally used from 1.5 to 6 times in excess. In phase synthesis, when a test using the ninhydrin reaction reveals that the condensation is insufficient, sufficient condensation can be conducted by repeating the condensation reaction without elimination of protecting groups. If the condensation is yet insufficient even after repeating the reaction, unreacted amino acids can be acylated with acetic anhydride, acetylimidazole or the like so that an influence on the subsequent reactions can be avoided.

Examples of the protecting groups for the amino groups of the starting amino acid include Z, Boc, tert-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, trityl and the like.

Examples of the carboxyl-protecting group for the starting amino acid include allyl, 2-adamantyl, 4-nitrobenzyl, 4-methoxybenzyl, 4-chlorobenzyl, phenacyl and benzyloxycarbonylhydrazide, tert-butoxycarbonylhydrazide, tritylhydrazide and the like, in addition to the above-mentioned $C_{1-6}$ alkyl group, $C_{3-10}$ cycloalkyl group, $C_{7-14}$ aralkyl group.

The hydroxyl group of serine or threonine can be protected, for example, by esterification or etherification. Examples of the group suitable for the esterification include lower ($C_{2-4}$) alkanoyl groups such as an acetyl group and the like, aroyl groups such as a benzoyl group and the like, and the like, and a group derived from an organic acid and the like. In addition, examples of the group suitable for etherification include benzyl, tetrahydropyranyl, tert-butyl($Bu^t$), trityl (Trt) and the like.

Examples of the protecting group for the phenolic hydroxyl group of tyrosine include Bzl, 2,6-dichlorobenzyl, 2-nitrobenzyl, Br—Z, tert-butyl and the like.

Examples of the protecting group for the imidazole of histidine include Tos, 4-methoxy-2,3,6-trimethylbenzenesulfonyl (Mtr), DNP, Bom, Bum, Boc, Trt, Fmoc and the like.

Examples of the protecting group for the guanidino group of arginine include Tos, Z, 4-methoxy-2,3,6-trimethylbenzenesulfonyl (Mtr), p-methoxybenzenesulfonyl (MBS), 2,2,5,7,8-pentamethylchromane-6-sulfonyl (Pmc), mesitylene-2-sulfonyl (Mts), 2,2,4,6,7-pentamethyldihydrobenzofuran-5-sulfonyl (Pbf), Boc, Z, $NO_2$ and the like.

Examples of the protecting group for a side chain amino group of lysine include Z, Cl—Z, trifluoroacetyl, Boc, Fmoc, Trt, Mtr, 4,4-dimethyl-2,6-dioxocyclohexylideneyl (Dde) and the like.

Examples of the protecting group for indolyl of tryptophan include formyl (For), Z, Boc, Mts, Mtr and the like.

Examples of the protecting group for asparagine and glutamine include Trt, xanthyl (Xan), 4,4'-dimethoxybenzhydryl (Mbh), 2,4,6-trimethoxybenzyl (Tmob) and the like.

Examples of activated carboxyl groups in the starting material include corresponding acid anhydride, azide, active esters [ester with alcohol (e.g., pentachlorophenol, 2,4,5-trichlorophenol, 2,4-dinitrophenol, cyanomethylalcohol, paranitrophenol, HONB, N-hydroxysuccimide, 1-hydroxybenzotriazole (HOBt), 1-hydroxy-7-azabenzotriazole (HOAt))] and the like. Examples of the activated amino group in the starting material include corresponding phosphorous amide.

Examples of the method for removing (eliminating) a protecting group include a catalytic reduction in a hydrogen stream in the presence of a catalyst such as Pd-black or Pd-carbon; an acid treatment using anhydrous hydrogen fluoride, methanesulfonic acid, trifluoromethanesulfonic acid, trifluoroacetate, trimethylsilyl bromide (TMSBr), trimethylsilyl trifluoromethanesulfonate, tetrafluoroboric acid, tris(trifluoro)boric acid, boron tribromide, or a mixture solution thereof; a base treatment using diisopropylethylamine, triethylamine, piperidine, piperazine or the like; and reduction with sodium in liquid ammonia, and the like. The elimination reaction by the above-described acid treatment is generally carried out at a temperature of −20° C. to 40° C.; the acid treatment is efficiently conducted by adding a cation scavenger such as anisole, phenol, thioanisole, metacresol and paracresol; dimethylsulfide, 1,4-butanedithiol, 1,2-ethanedithiol and the like. Also, a 2,4-dinitrophenyl group used as a protecting group of the imidazole of histidine is removed by thiophenol treatment; a formyl group used as a protecting group of the indole of tryptophan is removed by deprotection by acid treatment in the presence of 1,2-ethanedithiol, 1,4-butanedithiol, or the like, as well as by alkali treatment with dilute sodium hydroxide, dilute ammonia, or the like.

Protection of a functional group that should not be involved in the reaction of a starting material and a protecting group, elimination of the protecting group, activation of a functional group involved in the reaction and the like can be appropriately selected from known protecting groups and known means.

In a method of preparing an amide of the peptide, it is formed by a solid phase synthesis using a resin for amide synthesis, or the α-carboxyl group of the carboxy terminal amino acid is amidated, and a peptide chain is elongated to a desired chain length toward the amino group side, thereafter a peptide wherein the protecting group for the N-terminal α-amino group of the peptide chain only removed and a peptide wherein the protecting group for the C-terminal carboxyl group only removed of the peptide chain are prepared, and the both peptides are condensed in a mixed solvent described above. For details about the condensation reaction, the same as above applies. After the protected peptide obtained by the condensation is purified, all protecting groups can be removed by the above-described method to yield a desired crude polypeptide. By purifying this crude peptide using various publicly known means of purification, and freeze-drying the main fraction, a desired amide of the peptide can be prepared.

When the compound (I) is present as a configurational isomer such as enantiomer, diastereomer etc., a conformer or the like, they are also encompassed in compound (I) and each can be isolated by a means known per se or the above separation and purification methods on demand. In addition, when the compound (I) is in the form of a racemate, it can be separated into S- and R-forms by conventional optical resolution.

When the compound (I) includes stereoisomers, both the isomers alone and mixtures of each isomers are also encompassed in compound (I).

Compound (I) can be chemically modified according to a method known per se and using polyethylene glycol. For example, chemically modified compound (I) can be produced by conjugatedly binding polyethylene glycol to Cys residue, Asp residue, Glu residue, Lys residue and the like of compound (I).

Compound (I) modified by polyethylene glycol (PEG) produces, for example, the effects of promoting the biological activity, prolonging the blood circulation time, reducing the immunogenicity, enhancing the solubility, and enhancing the resistance to metabolism, of a therapeutically and diagnostically important peptide.

The molecular weight of PEG is not particularly limited and is normally about 1 K to about 1000 K daltons, preferably about 10 K to about 100 K daltons, more preferably about 20 K to about 60 K daltons.

A method well known in the art can be used as a method for modifying compound (I) by PEG, and, for example, the methods described below can be used.

(1) A PEGylating reagent having an active ester (e.g., SUNBRIGHT MEGC-30TS (trade name), NOF Corp.) is bound to the amino group of compound (I).
(2) A PEGylating reagent having an aldehyde (e.g., SUNBRIGHT ME-300AL (trade name), NOF Corp.) is bound to the amino group of compound (I).
(3) A divalent cross-linking reagent (e.g., GMBS (Dojindo Laboratories), EMCS (Dojindo Laboratories), KMUS (Dojindo Laboratories), SMCC (Pierce)) is bound to compound (I), to which a PEGylating reagent having a thiol group (e.g., SUNBRIGHT ME-300-SH (trade name), NOF Corp.) is then bound.
(4) A thiol group is introduced to compound (I) through an SH-introducing agent (e.g., D-cysteine residue, L-cysteine residue, Traut's reagent), and this thiol group is reacted with a PEGylating reagent having a maleimide group (e.g., SUNBRIGHT ME-300MA (trade name), NOF Corp.).
(5) A thiol group is introduced to compound (I) through an SH-introducing agent (e.g., D-cysteine residue, L-cysteine residue, Traut's reagent), and this thiol group is reacted with a PEGylating reagent having an iodoacetamide group (e.g., SUNBRIGHT ME-300IA (trade name), NOF Corp.).
(6) A ω-aminocarboxylic acid or an α-amino acid is introduced as a linker to the N-terminal amino group of compound (I), and an amino group derived from this linker is reacted with a PEGylating reagent having an active ester (e.g., SUNBRIGHT MEGC-30TS (trade name), NOF Corp.).
(7) A ω-aminocarboxylic acid or an α-amino acid is introduced as a linker to the N-terminal amino group of compound (I), and an amino group derived from this linker is reacted with a PEGylating reagent having an aldehyde group (e.g., SUNBRIGHT ME-300AL (trade name), NOF Corp.).

In addition, the compound (I) may be a solvate (e.g., hydrate) or a non-solvate (e.g., non-hydrate).

The compound (I) may be labeled with an isotope (e.g., $^3$H, $^{14}$C, $^{35}$S, $^{125}$I) or the like.

Furthermore, compound (I) may be a deuterium conversion form wherein $^1$H is converted to $^2$H(D).

Compound (I) labeled or substituted with an isotope can be used as, for example, a tracer (PET tracer) for use in Positron Emission Tomography (PET), and is useful in the fields of medical diagnosis and the like.

For the peptides mentioned herein, the left end is the N-terminal (amino terminal) and the right end is the C-terminal (carboxyl terminal) in accordance with the conventional peptide marking. The C-terminal of peptide may be any of an amide (—CONH$_2$), a carboxyl group (—COOH), a carboxylate (—COOO$^-$), an alkylamide (—CONHR$^a$), and an ester (—COOR$^a$). Particularly, amide (—CONH$_2$) is preferable.

Compound (I) may be in a salt form. Examples of such salt include metal salts, ammonium salts, salts with organic base, salts with inorganic acid, salts with organic acid, salts with basic or acidic amino acid, and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like. Preferable examples of the salt with acidic amino acid include salts with aspartic acid, glutamic acid and the like.

Among the above-mentioned salts, a pharmaceutically acceptable salt is preferable. For example, when a compound has an acidic functional group, an inorganic salt such as alkali metal salt (e.g., sodium salt, potassium salt etc.), alkaline earth metal salt (e.g., calcium salt, magnesium salt, barium salt etc.) and the like, ammonium salt etc., and when a compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, p-toluenesulfonic acid and the like are preferable.

Compound (I) may be in a prodrug form.

A prodrug means a compound which is converted to compound (I) with a reaction due to an enzyme, gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

Examples of a prodrug of compound (I) include a compound wherein an amino of compound (I) is acylated, alkylated or phosphorylated (e.g., compound wherein amino of compound (I) is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated or tert-butylated, and the like); a compound wherein a hydroxy of compound (I) is acylated, alkylated, phosphorylated or borated (e.g., a compound wherein a hydroxy of compound (I) is acetylated, palmitoylated, propanoylated, pivaloylated, succinylated, fumarylated, alanylated or dimethylaminomethylcarbonylated); a compound wherein a carboxy of compound (I) is esterified or amidated (e.g., a compound wherein a carboxy of compound (I) is $C_{1-6}$ alkyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated) and the like. Among others, a compound wherein carboxy of compound (I) is esterified with $C_{1-6}$ alkyl such as methyl, ethyl, tert-butyl or the like is preferably used. These compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

In the present specification, the prodrug may form a salt. Examples of such a salt include those exemplified as the salt of compound (I).

Compound (I) may be a crystal. Crystals having a singular crystal form or a mixture of plural crystal forms are also included in compound (I). Crystals can be produced by crystallizing compound (I) according to a crystallization method known per se.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

The crystal of compound (I) is superior in physicochemical properties (e.g., melting point, solubility, stability) and biological properties (e.g., pharmacokinetics (absorption, distribution, metabolism, excretion), efficacy expression), and thus it is extremely useful as a medicament.

Compound (I) and a prodrug thereof (hereinafter to be sometimes abbreviated as the compound of the present invention) have an activating action on GLP-1 receptors and GIP receptors.

The compound of the present invention has a high activating action on GLP-1 receptors and GIP receptors, particularly, in vivo.

GLP-1 and GIP are gut hormones called incretin, and have the action of promoting insulin secretion from the pancreas. Since incretin is closely related to glucose metabolism, the compound having an activating action on GLP-1 receptors and GIP receptors is useful in the prophylaxis or treatment of symptoms associated with glucose metabolism disorder, including obesity.

Thus, the compound of the present invention has a feeding suppressive action, weight increase inhibitory action and the like.

In addition, the compound of the present invention has superior solubility. The solubility of the compound of the present invention in water is preferably 1 mg/mL or higher, more preferably 10 mg/mL or higher.

The compound of the present invention can be used as an activator of a GLP-1 receptor and a GIP receptor (GLP-1 receptor/GIP receptor coagonist).

In the present invention, the activator of a GLP-1 receptor and a GIP receptor (GLP-1 receptor/GIP receptor coagonist) means an agent having both of a GLP-1 receptor-activating action (GLP-1 receptor agonist action) and a GIP receptor-activating action (GIP receptor agonist action). Specifically, the activator of a GLP-1 receptor and a GIP receptor (GLP-1 receptor/GIP receptor coagonist) means an agent wherein $EC_{50}$ against the GLP-1 receptor and $EC_{50}$ against the GIP receptor are 1:20 to 20:1, preferably 1:5 to 5:1.

The compound of the present invention has a low glucagon receptor-activating action (glucagon receptor agonist), and therefore has a low hyperglycemic action attributed thereto. $EC_{50}$ of the compound of the present invention against the glucagon receptor is 1/1000 or lower, preferably 1/10000 or lower, compared with $EC_{50}$ of the compound of the present invention against the GLP-1 receptor or the GIP receptor.

The compound of the present invention is low in its toxicity (e.g., acute toxicity, chronic toxicity, genetic toxicity, reproductive toxicity, cardiac toxicity, carcinogenicity), shows a few side effects, and can be safely administered to a mammal (e.g., human, bovine, horse, dog, cat, monkey, mouse, rat) as an agent for the prophylaxis or treatment of various diseases mentioned below and the like.

The compound of the present invention can be used as an agent for the treatment or prophylaxis of various diseases including obesity, by virtue of the above-mentioned activating action on GLP-1 receptors and GIP receptors. The compound of the present invention can be used as an agent for the prophylaxis or treatment of, for example, symptomatic obesity, obesity based on simple obesity, disease state or disease associated with obesity, eating disorder, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, low HDL-cholesterolemia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (disease states having 3 or more selected from hypertriglycerid(TG)emia, low HDL cholesterol(HDL-C)emia, hypertension, abdominal obesity and impaired glucose tolerance), sarcopenia and the like.

Examples of the symptomatic obesity include endocrine obesity (e.g., Cushing syndrome, hypothyroidism, insulinoma, obese type II diabetes, pseudohypoparathyroidism, hypogonadism), central obesity (e.g., hypothalamic obesity, frontal lobe syndrome, Kleine-Levin syndrome), hereditary obesity (e.g., Prader-Willi syndrome, Laurence-Moon-Biedl syndrome), drug-induced obesity (e.g., steroid, phenothiazine, insulin, sulfonylurea (SU) agent, β-blocker-induced obesity) and the like.

Examples of the disease state or disease associated with obesity include glucose tolerance disorders, diabetes (particularly type 2 diabetes, obese diabetes), lipid metabolism abnormality (synonymous with the above-mentioned hyperlipidemia), hypertension, cardiac failure, hyperuricemia-.gout, fatty liver (including non-alchoholic steato-hepatitis), coronary heart disease (myocardial infarction, angina pectoris), cerebral infarction (brain thrombosis, transient cerebral ischemic attack), bone/articular disease (knee osteoarthritis, hip osteoarthritis, spondylitis deformans, lumbago), sleep apnea syndrome/Pickwick syndrome, menstrual disorder (abnormal menstrual cycle, abnormality of menstrual flow and cycle, amenorrhea, abnormal catamenial symptom), metabolic syndrome and the like.

New diagnostic criteria were reported by The Japan Diabetes Society in 1999 about the diagnostic criteria of diabetes.

According to this report, diabetes refers to a state that meets any of a fasting blood glucose level (glucose concentration in venous plasma) of 126 mg/dl or more, a 2-hr value (glucose concentration in venous plasma) of 200 mg/dl or more in the 75 g oral glucose tolerance test (75 g OGTT), and a casual blood glucose level (glucose concentration in venous plasma) of 200 mg/dl or more. Also, a state that does not apply to the above-mentioned diabetes, and is not a state exhibiting "a fasting blood glucose level (glucose concentration in venous plasma) less than 110 mg/dl or a 2-hr value (glucose concentration in venous plasma) less than 140 mg/dl in the 75 g oral glucose tolerance test (75 g OGTT)" (normal type) is called "borderline type".

Moreover, new diagnostic criteria were reported by American Diabetes Association (ADA) in 1997 and by World Health Organization (WHO) in 1998 about the diagnostic criteria of diabetes.

According to these reports, diabetes refers to a state that meets a fasting blood glucose level (glucose concentration in venous plasma) of 126 mg/dl or more and a 2-hr value (glucose concentration in venous plasma) of 200 mg/dl or more in the 75 g oral glucose tolerance test.

According to the above-mentioned reports, impaired glucose tolerance refers to a state that meets a fasting blood glucose level (glucose concentration in venous plasma) less than 126 mg/dl and a 2-hr value (glucose concentration in venous plasma) of 140 mg/dl or more and less than 200 mg/dl in the 75 g oral glucose tolerance test. According to the report of ADA, a state exhibiting a fasting blood glucose level (glucose concentration in venous plasma) of 110 mg/dl or more and less than 126 mg/dl is called IFG (Impaired Fasting Glucose). On the other hand, according to the report of WHO, a state of the IFG (Impaired Fasting Glucose) exhibiting a 2-hr value (glucose concentration in venous plasma) less than 140 mg/dl in the 75 g oral glucose tolerance test is called IFG (Impaired Fasting Glycemia).

The compound of the present invention is also used as an agent for the prophylaxis or treatment of diabetes determined according to the above-mentioned new diagnostic criteria, borderline type diabetes, impaired glucose tolerance, IFG (Impaired Fasting Glucose) and IFG (Impaired Fasting Glycemia). Moreover, the compound of the present invention can prevent progress of borderline type, impaired glucose tolerance, IFG (Impaired Fasting Glucose) or IFG (Impaired Fasting Glycemia) into diabetes.

The compound of the present invention has the action of inhibiting weight increase, and as such, can be used as a weight increase inhibitor for mammals. A mammal that is subject to the application of the compound of the present invention can be a mammal desired to avoid weight increase. The mammal may be a mammal having a genetic risk of weight increase, or may be a mammal affected by lifestyle-related disease such as diabetes, hypertension and/or hyperlipidemia. The weight increase may be attributed to excessive ingestion of food or unbalanced diets, or may be weight increase derived from a concomitant drug (e.g., insulin sensitizers having a PPARγ agonist-like action, such as troglitazone, rosiglitazone, englitazone, ciglitazone, pioglitazone and the like). Alternatively, the weight increase may be weight increase before reaching obesity, or may be weight increase in obesity patients. Here, obesity is defined as a body mass index (BMI: body weight (kg) [height (m)]$^2$) of 25 or more (according to the criteria of Japan Society for the Study of Obesity) for Japanese and as BMI of 30 or more (according to the criteria of WHO) for Western people.

The compound of the present invention is also useful as an agent for the prophylaxis or treatment of metabolic syndrome. The incidence of cardiovascular disease is significantly high in metabolic syndrome patients, compared with patients with a single lifestyle-related disease. Thus, the prophylaxis or treatment of metabolic syndrome is exceedingly important for preventing cardiovascular disease.

The diagnostic criteria of metabolic syndrome were announced by WHO in 1999 and by NCEP in 2001. According to the diagnostic criteria of WHO, an individual having hyperinsulinemia or abnormal glucose tolerance as a requirement and two or more of visceral obesity, dyslipidemia (high TG or low HDL) and hypertension is diagnosed as having metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the diagnostic criteria of the Adult Treatment Panel III of the National Cholesterol Education Program (guideline of ischemic heart disease) in USA, an individual having three or more of visceral obesity, hypertriglyceridemia, low HDL-cholesterolemia, hypertension and abnormal glucose tolerance is diagnosed as having metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used as an agent for the prophylaxis or treatment of, for example, osteoporosis, cachexia (e.g., cancerous cachexia, tuberculous cachexia, diabetic cachexia, cachexia associated with blood disease, cachexia associated with endocrine disease, cachexia associated with infectious disease or cachexia caused by acquired immunodeficiency syndrome), fatty liver, polycystic ovary syndrome, renal disease (e.g., chronic renal failure, diabetic nephropathy, glomerulonephritis, glomerulosclerosis, Nephrotic syndrome, hypertensive nephrosclerosis, end-stage renal disease), muscular dystrophy, myocardial infarction, angina pectoris, cerebrovascular disorder (e.g., cerebral infarction, stroke), Alzheimer's disease, Parkinson's disease, anxiety, dementia, insulin resistant syndrome, syndrome X, hyperinsulinemia, paresthesia caused by hyperinsulinemia, acute or chronic diarrhea, inflammatory disease (e.g., chronic rheumatoid arthritis, spondylitis deformans, arthritis deformans, lumbago, gout, post-operational or post-traumatic inflammation, bloating, neuralgia, laryngopharyngitis, cystitis, hepatitis (including non-alcoholic steatohepatitis), pneumonia, pancreatitis, enteritis, inflammatory bowel disease (including inflammatory large bowel disease), colitis ulcerosa, gastric mucosal injury (including gastric mucosal injury caused by aspirin)), small intestinal mucosal injury, malabsorption, testicular dysfunction, visceral obesity syndrome and sarcopenia.

Moreover, the compound of the present invention can also be used as an agent for the prophylaxis or treatment of various cancers (particularly, breast cancer (e.g., invasive ductal breast cancer, noninvasive ductal breast cancer, inflammatory breast cancer, etc.), prostate cancer (e.g., hormone-dependent prostate cancer, hormone-independent prostate cancer, etc.), pancreatic cancer (e.g., ductal pancreatic cancer, etc.), gastric cancer (e.g., papillary adenocarcinoma, mucous adenocarcinoma, adenosquamous carcinoma, etc.), lung cancer (e.g., non-small cell lung cancer, small-cell lung cancer, malignant mesothelioma, etc.), colon cancer (e.g., gastrointestinal stromal tumor, etc.), rectal cancer (e.g., gastrointestinal stromal tumor, etc.), colorectal cancer (e.g., familial colorectal cancer, hereditary non-polyposis colorectal cancer, gastrointestinal stromal tumor, etc.), small intestinal cancer (e.g., non-Hodgkin's lymphoma, gastrointestinal stromal tumor, etc.), esophageal cancer, duodenal cancer, tongue cancer, pharyngeal cancer (e.g., nasopharyngeal cancer, oropharynx cancer, hypopharyngeal cancer, etc.), salivary gland cancer, brain tumor (e.g., pineal astrocytoma, pilocytic astrocytoma, diffuse astrocytoma, anaplastic astrocytoma, etc.), neurilemmoma, liver cancer (e.g., primary liver cancer, extrahepatic bile duct cancer, etc.), renal cancer (e.g., renal cell cancer, transitional cell cancer of the renal pelvis and ureter, etc.), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential, etc.), bladder cancer, urethral cancer, skin cancer (e.g., intraocular (ocular) melanoma, Merkel cell carcinoma, etc.), hemangioma, malignant lymphoma, malignant melanoma, thyroid cancer (e.g., medullary thyroid cancer, etc.), parathyroid cancer, nasal cavity cancer, sinus cancer, bone tumor (e.g., osteosarcoma, Ewing tumor, uterine sarcoma, soft tissue sarcoma, etc.), angiofibroma, sarcoma of the retina, penis cancer, testicular tumor, pediatric solid tumor (e.g., Wilms' tumor, childhood kidney tumor, etc.), Kaposi's sarcoma, Kaposi's sarcoma caused by AIDS, tumor of maxillary sinus, fibrous histiocytoma, leiomyosarcoma, rhabdomyosarcoma, leukemia (e.g., acute myeloid leukemia, acute lymphoblastic leukemia, etc.), etc.).

The compound of the present invention can also be used for secondary prevention or suppression of progression of the above-mentioned various diseases (e.g., cardiovascular events such as myocardial infarction and the like). In addition, the compound of the present invention is also useful as a feeding suppressant and a weight increase inhibitor. The compound of the present invention can also be used in combination with a diet therapy (e.g., diet therapy for diabetes), and an exercise therapy.

A medicament containing the compound of the present invention shows low toxicity and is obtained using the compound of the present invention alone or in admixture with a pharmacologically acceptable carrier according to a method known per se (e.g., the method described in the Japanese Pharmacopoeia) generally used as production methods of pharmaceutical preparations, and safely administered orally or parenterally (e.g., topically, rectally, intravenously administered) as a pharmaceutical preparation, for example, tablets (inclusive of sugar-coated tablets, film-coated tablets, sublingual tablets, orally disintegrating tablets), powders, granules, capsules (inclusive of soft capsules, microcapsules), liquids, troches, syrups, emulsions, suspensions, injections (e.g., subcutaneous injections, intravenous injections, intramuscular injections, intraperitoneal injections etc.), external preparations (e.g., transnasal preparations, dermal preparations, ointments), suppository (e.g., rectal suppositories, vaginal suppositories), pellets, nasal preparations, pulmonary preparations (inhalants), transfusions and the like.

These preparations may be controlled release preparations such as a rapid release preparation, a sustained release preparation and the like (e.g., a sustained release microcapsule).

The content of the compound of the present invention in a pharmaceutical preparation is about 0.01- about 100 wt % of the whole preparation.

The above-mentioned pharmaceutically acceptable carrier may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Further, if necessary, general additives such as preservative, antioxidant, colorant, sweetening agent, adsorbing agent, wetting agent and the like can be also used appropriately in a suitable amount.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoic acid esters, chlorobutanol, benzyl alcohol, phenethyl alcohol, dehydroacetic acid, sorbic acid and the like.

Examples of the antioxidant include sulfites, ascorbic acid, α-tocopherol and the like.

Examples of the colorant include water-soluble Food coal tar dyes (e.g., Food dyes such as Food Red No. 2 and No. 3, Food Yellow No. 4 and No. 5, Food Blue No. 1 and No. 2, and the like), water-insoluble lake dyes (e.g., aluminum salts of the aforementioned water-soluble Food coal tar dyes), natural dyes (e.g., β-carotene, chlorophyll, ferric oxide red) and the like.

Examples of the sweetening agent include saccharin sodium, dipotassium glycyrrhizinate, aspartame, stevia and the like.

Examples of the adsorbing include porous starch, calcium silicate (trade name: Florite RE), magnesium alumino metasilicate (trade name: Neusilin) and light anhydrous silicic acid (trade name: Sylysia).

Examples of the wetting agent include propylene glycol monostearate, sorbitan monooleate, diethylene glycol monolaurate and polyoxyethylenelauryl ether.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The dosage of the compound of the present invention is appropriately determined according to the subject of administration, symptom, administration method and the like. For example, when the compound of the present invention is administered orally to an obesity or diabetes patient (body weight 60 kg), the daily dose of the compound of the present invention is about 0.1 to 100 mg, preferably about 1.0 to 50 mg, more preferably about 1.0 to 20 mg. When the compound of the present invention is administered parenterally to an obesity or diabetes patient (body weight 60 kg), the daily dose of the compound of the present invention is about 0.01 to 30 mg, preferably about 0.1 to 20 mg, more preferably about 0.5 to 10 mg. These amounts can be administered in about 1 to several portions a day.

The compound of the present invention can be administered, for example, every day (once per day, twice per day, 3 times per day, 4 times per day, 5 times per day, 6 times per day), every 2 days, every 3 days, every 4 days, every 5 days, every 6 days, every week, twice per week, every other week, every 3 weeks, every month, every 2 months, every 3 months, every 4 months, every 5 months or every 6 months.

The compound of the present invention can be used in combination with other drug that does not adversely influence the compound of the present invention, for the purpose of, for example, promoting the action (treatment of effect for obesity, diabetes and the like) of the compound of the present invention, reducing the dose of the compound of the present invention, and the like.

Examples of a drug that can be used in combination with the compound of the present invention (hereinafter sometimes to be abbreviated as a concomitant drug) include anti-obesity agents, therapeutic agents for diabetes, therapeutic agents for diabetic complications, therapeutic agents for hyperlipidemia, antihypertensive agents, diuretics, chemotherapeutics, immunotherapeutics, anti-inflammatory drugs, antithrombotic agents, therapeutic agents for osteoporosis, vitamins, antidementia drugs, erectile dysfunction drugs, therapeutic drugs for urinary frequency or urinary incontinence, therapeutic agents for dysuria and the like. Specific examples of the concomitant drug include those mentioned below.

Examples of the anti-obesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor modulator, GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFK inhibitory (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21), anorexigenic agents (e.g., P-57) and the like.

Here, as the therapeutic agent for diabetes, for example, insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably, hydrochloride), rosiglitazone or a salt thereof (preferably, maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in W0007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, Trelagliptin or a salt thereof (preferably succinate)), β3 agonists (e.g., N-5984), GPR40 agonists (e.g., Fasiglifam or a hydrate thereof, compound described in WO2004/041266, WO2004/106276, WO2005/063729, WO2005/063725, WO2005/087710, WO2005/095338, WO2007/013689 or WO2008/001931), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in W0006/112549, W0007/028135, W0008/047821, W0008/050821, W0008/136428 or W0008/156757), GPR119 agonists (e.g., PSN821, MBX-2982, APD597), FGF21, FGF analogue, ACC2 inhibitors and the like can be mentioned.

As the therapeutic agent for diabetic complications, aldose reductase inhibitors (e.g., tolrestat, epalrestat, zopolrestat, fidarestat, CT-112, ranirestat (AS-3201), lidorestat), neurotrophic factor and increasing agents thereof (e.g., NGF, NT-3, BDNF, neurotrophic production/secretion promoting agent described in WO01/14372 (e.g., 4-(4-chlorophenyl)-2-(2-methyl-1-imidazolyl)-5-[3-(2-methylphenoxy)propyl] oxazole), compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like can be mentioned.

As the therapeutic agent for hyperlipidemia, HMG-COA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), probucol, nicotinic acid drugs (e.g., nicomol, niceritrol, niaspan), ethyl icosapentate, phytosterol (e.g., soysterol, gamma oryzanol (γ-oryzanol)), cholesterol absorption inhibitors (e.g., zechia), CETP inhibitors (e.g., dalcetrapib, anacetrapib), ω-3 fatty acid preparations (e.g., ω-3-fatty acid ethyl esters 90 (ω-3-acid ethyl esters 90)) and the like can be mentioned.

Examples of the antihypertensive agent include angiotensin converting enzyme inhibitors (e.g., captopril, enalapril, delapril, etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil, etc.), calcium antagonists (e.g., manidipine, nifedipine, amlodipine, efonidipine, nicardipine, cilnidipine, etc.), β blockers (e.g., metoprolol, atenolol, propranolol, carvedilol, pindolol, etc.), clonidine and the like.

As the diuretic, for example, xanthine derivatives (e.g., theobromine sodium salicylate, theobromine calcium salicylate and the like), thiazide preparations (e.g., ethiazide, cyclopenthiazide, trichloromethiazide, hydrochlorothiazide, hydroflumethiazide, benzylhydrochlorothiazide, penfluthiazide, poly5thiazide, methyclothiazide and the like), antialdosterone preparations (e.g., spironolactone, triamterene and the like), carbonic anhydrase inhibitors (e.g., acetazolamide and the like), chlorobenzenesulfonamide agents (e.g., chlortalidone, mefruside, indapamide and the like), azosemide, isosorbide, ethacrynic acid, piretanide, bumetanide, furosemide and the like can be mentioned.

Examples of the chemotherapeutic include alkylating agents (e.g., cyclophosphamide, ifosfamide), antimetabolites (e.g., methotrexate, 5-fluorouracil), anticancer antibiotics (e.g., mitomycin, adriamycin), plant-derived anticancer agents (e.g., vincristine, vindesine, Taxol), cisplatin, carboplatin, etoposide and the like. Among others, a 5-fluorouracil derivative Furtulon or Neofurtulon or the like is preferable.

Examples of the immunotherapeutic include microbial or bacterial components (e.g., muramyl dipeptide derivative, Picibanil), polysaccharides having immunoenhancing activity (e.g., lentinan, sizofiran, Krestin), cytokines obtained by genetic engineering approaches (e.g., interferon, interleukin (IL)), colony-stimulating factors (e.g., granulocyte colony-stimulating factor, erythropoietin) and the like. Among others, interleukins such as IL-1, IL-2, IL-12 and the like are preferable.

Examples of the anti-inflammatory drug include nonsteroidal anti-inflammatory drugs such as aspirin, acetaminophen, indomethacin and the like.

As the antithrombotic agent, for example, heparin (e.g., heparin sodium, heparin calcium, enoxaparin sodium, dalteparin sodium), warfarin (e.g., warfarin potassium), antithrombin drugs (e.g., aragatroban, dabigatran), FXa inhibitors (e.g., rivaroxaban, apixaban, edoxaban, YM150, compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like can be mentioned.

Examples of the therapeutic agent for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamin include vitamin $B_1$, vitamin $B_{12}$ and the like.

Examples of the antidementia drug include tacrine, donepezil, rivastigmine, galanthamine and the like.

Examples of the erectile dysfunction drug include apomorphine, sildenafil citrate and the like.

Examples of the therapeutic drug for urinary frequency or urinary incontinence include flavoxate hydrochloride, oxybutynin hydrochloride, propiverine hydrochloride and the like.

Examples of the therapeutic agent for dysuria include acetylcholine esterase inhibitors (e.g., distigmine) and the like.

Moreover, a drug confirmed to have a cachexia-ameliorating action either in animal models or clinically, i.e., a cyclooxygenase inhibitor (e.g., indomethacin), a progesterone derivative (e.g., megestrol acetate), glucocorticoid (e.g., dexamethasone), a metoclopramide drug, a tetrahydrocannabinol drug, an agent for improving fat metabolism (e.g., eicosapentaenoic acid), growth hormone, IGF-1, or an antibody against a cachexia-inducing factor TNF-α, LIF, IL-6 or oncostatin M or the like can also be used in combination with the compound of the present invention.

Alternatively, a glycation inhibitor (e.g., ALT-711), a nerve regeneration-promoting drug (e.g., Y-128, VX853, prosaptide), an antidepressant (e.g., desipramine, amitriptyline, imipramine), an antiepileptic drug (e.g., lamotrigine, Trileptal, Keppra, Zonegran, Pregabalin, Harkoseride, carbamazepine), an antiarrhythmic drug (e.g., mexiletine), an acetylcholine receptor ligand (e.g., ABT-594), an endothelin receptor antagonist (e.g., ABT-627), a monoamine uptake inhibitor (e.g., tramadol), a narcotic analgesic (e.g., morphine), a GABA receptor agonist (e.g., gabapentin, MR preparation of gabapentin), an α2 receptor agonist (e.g., clonidine), a local analgesic (e.g., capsaicin), an antianxiety drug (e.g., benzothiazepine), a phosphodiesterase inhibitor (e.g., sildenafil), a dopamine receptor agonist (e.g., apomorphine), midazolam, ketoconazole or the like may be used in combination with the compound of the present invention.

The time of administration of the compound of the present invention and that of the concomitant drug are not limited, and they may be administered simultaneously or in a staggered manner to the administration subject.

Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, symptom, administration method, target disease, combination and the like. When the subject of administration is human, for example, a concomitant drug can be used in 0.01-100 parts by weight relative to 1 part by weight of the compound of the present invention.

By combining the compound of the present invention and concomitant drug:
(1) the dose of the compound of the present invention or a concomitant drug can be reduced as compared to single administration of the compound of the present invention or a concomitant drug,
(2) the drug to be used in combination with the compound of the present invention can be selected depending on the condition of patients (mild, severe and the like), (3) the period of treatment can be set longer by selecting a concomitant drug having different action and mechanism from those of the compound of the present invention,
(4) a sustained treatment effect can be designed by selecting a concomitant drug having different action and mechanism from those of the compound of the present invention,
(5) a synergistic effect can be afforded by a combined use of the compound of the present invention and a concomitant drug, and the like, can be achieved.

EXAMPLES

The abbreviations used in the present specification mean the following (Table 1-1 and Table 1-2). A hyphen in terms such as α-MePhe and the like as described herein may be omitted, and the event of omission also represents the same meaning.

TABLE 1-1

| | |
|---|---|
| Aad | 2-aminoadipic acid |
| Abu | 2-aminobutyric acid |
| Abz(2) | 2-aminobenzoic acid |
| Ac | acetyl |
| Acp | 6-aminocaproic acid |
| Acpc | 1-aminocyclopropanecarboxylic acid |
| Adc(12) | 12-aminododecanic acid |
| Aib | α-aminoisobutyric acid |
| Aipe | 3-aminobutyric acid |
| Ala(4Pip) | 4-piperidinylalanine |
| Ala(cPr) | cyclopropylalanine |
| Alb | Albizziin 2-amino-3-ureidopropionic acid |
| Ambz(4) | 4-aminomethylbenzoyl |
| Aoc(8) | 8-aminocaprylic acid |
| Arg(Me) | Nω-methylarginine |
| Asn(Me) | Nω-methylasparagine |
| Aze(2) | azetidine-2-carboxylic acid |
| Aze(3) | azetidine-3-carboxylic acid |
| CC(Acp) | 6-carboxypentylcarbamoyl |
| CC(β-Ala) | 2-carboxyethylcarbamoyl |
| CC(GABA) | 3-carboxypropylcarbamoyl |
| CC(Gly) | carboxymethylcarbamoyl |
| CC(Leu) | [(1S)-1-carboxy-3-methylbutyl]carbamoyl |
| CC(Ser) | [(1S)-1-carboxy-2-hydroxyethyl]carbamoyl |
| CC(Tyr) | [(1S)-1-carboxy-2-(4-hydroxyphenyl)ethyl]carbamoyl |
| Cha | cyclohexylalanine |
| cisHyp | cis-4-hydroxyproline |
| Cit | citrulline |
| cPrCO | cyclopropanecarbonyl |
| Dab | 2,4-diaminobutyric acid |
| Dap | 2,3-diaminopropionic acid |
| GABA | γ-aminobutyric acid |
| Gly(cPr) | cyclopropylglycine |
| Gly-ψ[(E)CH═CH]-Leu | —CONH— bond between Gly and Leu is substituted by (E) type alkene |
| Har | homoarginine |
| homoLeu | homoleucine |
| Hse | homoserine |
| Hyp | trans-4-hydroxyproline |
| Iva | isovaline |
| Leu(Me) | γ-methylleucine |

TABLE 1-1-continued

| | |
|---|---|
| Lys(Ac) | Nε-acetyllysine |
| Lys(Hexyl) | Nε-hexyllysine |
| Lys(Me) | Nε-methyllysine |
| Lys(Me2) | Nε,ε-dimethyllysine |

Val or V::valine
Leu or L::leucine
Ile or I::isoleucine
Ser or S::serine
Thr or T::threonine
Cys or C::cysteine
Met or M::methionine

TABLE 1-2

| | |
|---|---|
| Lys[Hexadecanoyl-(PEG2)] | 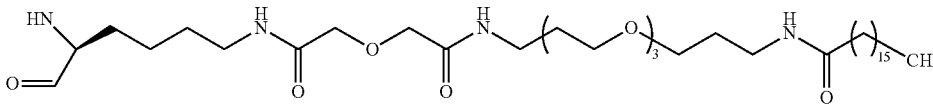 |
| N(2-hydroxyethyl)Gly | N-(2-hydroxyethyl)glycine |
| N(iBu)Gly | N-isobutylglycine |
| Nal(1) | 1-naphthylalanine |
| Nal(2) | 2-naphthylalanine |
| Nar | Norarginine |
| Nle | Norleucine |
| NmeAla | Nα-methylalanine |
| NmeSer | Nα-methylserine |
| NmePhe | Nα-methylphenylalanine |
| Nva | Norvaline |
| Orn | ornithine |
| PEG2 | 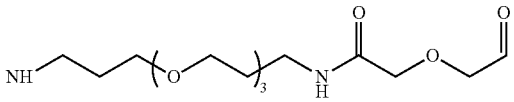 |
| Phe(2,6-Me$_2$)lat | 2,6-dimethylphenylalanine |
| Phe(2F) | 2-fluorophenylalanine |
| Phe(2Me) | 2-methylphenylalanine |
| Phe(3F) | 3-fluorophenylalanine |
| Phe(3Me) | 3-methylphenylalanine |
| Phe(4Cl) | 4-chlorophenylalanine |
| Phe(4F) | 4-fluorophenylalanine |
| Phe(4Me) | 4-methylphenylalanine |
| Phe(4NH$_2$) | 4-aminophenylalanine |
| Phg | phenylglycine |
| Pic(2) | 2-piperidinecarboxylic acid |
| Pic(4) | 4-piperidinecarboxylic acid |
| Pya(2) | 2-pyridylalanine |
| Pya(3) | 3-pyridylalanine |
| Pya(4) | 4-pyridylalanine |
| 4-PyCO | 4-pyridylcarbonyl |
| Ser(Me) | O-methylserine |
| Thp(4) | tetrahydro-2H-pyran-4-yl |
| Thr(Me) | O-methylthreonine |
| threo-PhSer | threo-3-phenylserine |
| Tic | 1,2,3,4-tetrahydroisoquinoline-3-carboxylic acid |
| Tyr(2F) | 2-fluorotyrosine |
| Tyr(3F) | 3-fluorotyrosine |
| Tyr(Me) | O-methyltyrosine |
| Z | benzyloxycarbonyl |
| α-MePhe | α-methylphenylalanine |
| α-MePro | α-methylproline |
| β-Ala | β-alanine |
| β-HOAla | β-homoalanine |

In the specification, where bases, amino acids, etc. are denoted by their codes, they are based on conventional codes in accordance with the IUPAC-IUB Commission on Biochemical Nomenclature or by the common codes in the art, examples of which are shown below. For amino acids that may have an optical isomer, L-form is presented unless otherwise indicated (e.g., "Ala" is L-form of Ala). In addition, "D-" means a D-form (e.g., "D-Ala" is D-form of Ala), and "DL-" means a racemate of a D-form and an L-form (e.g., "DL-Ala" is DL racemate of Ala).

TFA::trifluoroacetic acid
Gly or G::glycine
Ala or A::alanine
Glu or E::glutamic acid
Asp or D::aspartic acid
Lys or K::lysine
Arg or R::arginine
His or H::histidine
Phe or F::phenylalanine
Tyr or Y::tyrosine
Trp or W::tryptophan
Pro or P::proline
Asn or N::asparagine
Gln or Q::glutamine
pGlu::pyroglutamic acid
α-MeTyr::α-methyltyrosine The present invention is explained in detail in the following by referring to the following Reference Examples, Examples, Test Examples and Formulation Examples, which are mere embodiments and not to be construed as limitative. In addition, the present invention may be modified without departing from the scope of invention.

The term "room temperature" in the following Examples indicates the range of generally from about 10° C. to about 35° C. As for "%", the yield is in mol/mol %, the solvent used for chromatography is in % by volume and other % is in % by weight.

THF: tetrahydrofuran
DMF: N,N-dimethylformamide
WSC: 1-(3-dimethylaminopropyl)-3-ethylcarbodiimide hydrochloride
HOBt: 1-hydroxybenzotriazole monohydrate Reference Example 1

Synthesis of H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10)

Sieber amide resin (0.69 meq/g, 362 mg) was added to a reaction tube, which was then loaded in a peptide synthesizer. Amino acids were successively condensed according to the Fmoc/DCC/HOBt protocol. In the final step, the N-terminal Fmoc group was removed. After the termination of condensation, the resin was washed with MeOH, and dried under reduced pressure. As a result, 1025 mg (0.244 meq/g) of the protected peptide resin of interest was obtained.

Reference Example 2

Synthesis of H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Sieber amide resin (SEQ ID NO: 11)

Sieber amide resin (0.69 meq/g, 362 mg) was added to a reaction tube, which was then loaded in a peptide synthesizer. Amino acids were successively condensed according to the Fmoc/DCC/HOBt protocol. In the final step, the N-terminal Fmoc group was removed. After the termination of condensation, the resin was washed with MeOH, and dried under reduced pressure. As a result, 1331 mg (0.188 meq/g) of the protected peptide resin of interest was obtained.

Reference Example 3

Synthesis of H-Ala-Gln(Trt)-Ala-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 12)

Sieber amide resin (0.61 meq/g, 410 mg) was added to a reaction tube, which was then loaded in a peptide synthesizer. Amino acids were successively condensed according to the Fmoc/DCC/HOBt protocol. Double coupling was performed for introducing 18-position and 20-position Ala and 19-position Gln(Trt). In the final step, the N-terminal Fmoc group was removed. After the termination of condensation, the resin was washed with MeOH, and dried under reduced pressure. As a result, 1110 mg (0.225 meq/g) of the protected peptide resin of interest was obtained.

Example 1

Synthesis of H-Tyr-Aib-Glu-Gly-Thr-αMePhe-Thr-Ser-Asp-Tyr-Ala-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$
(SEQ ID NO: 13)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin(SEQ ID NO: 10) (0.244 meq/g, 41.0 mg) prepared in Reference Example 1 was weighed into a reaction tube, and swollen with DMF. After removal of DMF by filtration, Fmoc-Ala-OH (31.1 mg), 0.5 M OxymaPure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Ala, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 83 mg of H-Tyr(tBu)-Aib-Glu(OtBu)-Gly-Thr(tBu)-αMePhe-Thr(tBu)-Ser(tBu)-Asp(OtBu)-Tyr(tBu)-Ala-Ile-Aib-Leu-Asp(OtBu)-Lys(Boc)-Gln(Trt)-Ala-Gln(Trt)-Ala-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)- Lys(Boc)-Sieber amide resin(SEQ ID NO: 39).

To 83 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-0DS-P column (250×20 mm I.D.) [Solution A: 0.1% TFA-water, Solution B: 0.1% TFA-containing acetonitrile, flow rate 8 mL/min, A/B: 65/35-55/45 linear concentration gradient elution (60 min)]. The fractions containing the object product were collected and freeze-dried to give 22.5 mg of a white powder.

Mass spectrometry, (M+H)$^+$4267.4 (Calculated: 4267.2)
HPLC elution time: 7.1 min
elution condition:
column: Merck Chromolith Performance RP-18e (100×4.6 mm I.D.)
eluent: using Solution A: 0.1% TFA-water, Solution B: 0.1% TFA-containing acetonitrile, A/B: 95/5-35/65 linear concentration gradient elution (10 min)
flow rate: 3.0 mL/min

Example 2

Synthesis of H-Tyr-Aib-Glu-Gly-Thr-αMePhe-Thr-Ser-Asp-Tyr-Aib-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 14)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin(SEQ ID NO: 10) (0.244 meq/g, 41.0 mg) prepared in Reference Example 1 was weighed into a reaction tube, and swollen with DMF. After removal of DMF by filtration, Fmoc-Ala-OH (31.1 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 84.5 mg of H-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ala-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin(SEQ ID NO: 40).

To 84.5 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 65/35-55/45 linear concentration gradient elution (60 min)]. The fractions containing the object product were collected and freeze-dried to give 21.5 mg of a white powder.

Mass spectrometry, (M+H)$^+$4281.5 (Calculated: 4281.2)
HPLC elution time: 7.2 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 3

Synthesis of H-Tyr-Aib-Glu-Gly-Thr-αMePhe-Thr-Ser-Asp-Tyr-Ala-Ile-Aib-Leu-Asp-Lys-Gln-Ala-Gln-Ser-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 15)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.244 meq/g, 41.0 mg) prepared in Reference Example 1 was weighed into a reaction tube, and swollen with DMF. After removal of DMF by filtration, Fmoc-Ser(tBu)-OH (38.3 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Ala, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 73.3 mg of H-Tyr(tBu)-Aib-Glu(OtBu)-Gly-Thr(tBu)-αMePhe-Thr(tBu)-Ser(tBu)-Asp(OtBu)-Tyr(tBu)-Ala-Ile-Aib-Leu-Asp(OtBu)-Lys(Boc)-Gln(Trt)-Ala-Gln(Trt)-Ser(tBu)-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin(SEQ ID NO: 41).

To 73.3 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 65/35-55/45 linear concentration gradient elution (60 min)]. The fractions containing the object product were collected and freeze-dried to give 17.1 mg of a white powder.

Mass spectrometry, (M+H)$^+$4283.6 (Calculated: 4283.2)
HPLC elution time: 7.1 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 4

Synthesis of H-Tyr-Aib-Glu-Gly-Thr-αMePhe-Thr-Ser-Asp-Tyr-Aib-Ile-Aib-Leu-Asp-Lys-Gln-Ala-Gln-Ser-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 16)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.244 meq/g, 41.0 mg) prepared in Reference Example 1 was weighed into a reaction tube, and swollen with DMF. After removal of DMF by filtration, Fmoc-Ser(tBu)-OH (38.3 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 63 mg of H-Tyr(tBu)-Aib-Glu(OtBu)-Gly-Thr(tBu)-αMePhe-Thr (tBu)-Ser (tBu)-Asp (OtBu)-Tyr (tBu)-Aib-Ile-Aib-Leu-Asp (OtBu)-Lys (Boc)-Gln (Trt)-Ala-Gln (Trt)-Ser (tBu)-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin(SEQ ID NO: 42).

To 63 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 64/36-54/46 linear concentration gradient elution (60 min)]. The fractions containing the object product were collected and freeze-dried to give 14.7 mg of a white powder.

Mass spectrometry, (M+H)$^+$ 4297.8 (Calculated: 4297.2) HPLC elution time: 7.2 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 5

Synthesis of H-Tyr-Aib-Glu-Gly-Thr-αMePhe-Thr-Ser-Asp-Tyr-Ala-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-NH$_2$ (SEQ ID NO: 17)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Sieber amide resin (SEQ ID NO: 11) (0.188 meq/g, 53.2 mg) prepared in Reference Example 2 was weighed into a reaction tube, and swollen with DMF. After removal of DMF by filtration, Fmoc-Ala-OH (31.1 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Ala, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 97 mg of H-Tyr(tBu)-Aib-Glu(OtBu)-Gly-Thr(tBu)-αMePhe-Thr(tBu)-Ser(tBu)-Asp(OtBu)-Tyr(tBu)-Ala-Ile-Aib-Leu-Asp(OtBu)-Lys(Boc)-Gln(Trt)-Ala-Gln(Trt)-Ala-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)- Sieber amide resin (SEQ ID NO: 43).

To 97 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 63/37-53/47 linear concentration gradient elution (60 min)]. The fractions containing the object product were collected and freeze-dried to give 25.2 mg of a white powder.

Mass spectrometry, (M+H)$^+$ 4139.2 (Calculated: 4139.1) HPLC elution time: 7.3 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 6

Synthesis of H-Tyr-Aib-Glu-Gly-Thr-αMePhe-Thr-Ser-Asp-Tyr-Aib-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-NH$_2$ (SEQ ID NO: 18)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Sieber amide resin (SEQ ID NO: 11) (0.188 meq/g, 53.2 mg) prepared in Reference Example 2 was weighed into a reaction tube, and swollen with DMF. After removal of DMF by filtration, Fmoc-Ala-OH (31.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 78.1 mg of H-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ala-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)- Sieber amide resin (SEQ ID NO: 44).

To 78.1 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 63/37-53/47 linear concentration gradient elution (60 min)]. The fractions containing the object product were collected and freeze-dried to give 18.4 mg of a white powder.

Mass spectrometry, (M+H)$^+$4152.9 (Calculated: 4153.1) HPLC elution time: 7.4 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 7

Synthesis of H-Tyr-Aib-Glu-Gly-Thr-αMePhe-Thr-Ser-Asp-Tyr-Ala-Ile-Aib-Leu-Asp-Lys-Gln-Ala-Gln-Ser-Glu-Phe-Val-Lys-Trp-Leu-Leu-Lys-Gly-Gly-Pro-Ser-Ser-Gly-Ala-Pro-Pro-Pro-Ser-NH$_2$ (SEQ ID NO: 19)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Sieber amide resin (SEQ ID NO: 11) (0.188 meq/g, 53.2 mg) prepared in Reference Example 2 was weighed into a reaction tube, and swollen with DMF. After removal of DMF by filtration, Fmoc-Ser(tBu)-OH (38.3 mg), 0.5 M Oxymapure in DMF (200 μL) and diisopropylcarbodiimide (15.9 μL, 0.1 mmol) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Ala, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 87 mg of H-Tyr(tBu)-Aib-Glu(OtBu)-Gly-Thr(tBu)-αMePhe-Thr(tBu)-Ser (tBu)-Asp (OtBu)-Tyr (tBu)-Ala-Ile-Aib-Leu-Asp(OtBu)-Lys (Boc)-Gln (Trt)-Ala-Gln (Trt)-Ser (tBu)-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Sieber amide resin(SEQ ID NO: 45).

To 87 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 65/35-55/45 linear concentration gradient elution (60 min)]. The fractions containing the object product were collected and freeze-dried to give 17 mg of a white powder.

Mass spectrometry, (M+H)$^+$4154.8 (Calculated: 4155.1) HPLC elution time: 7.3 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 8

Synthesis of H-Tyr-Aib-Glu-Gly-Thr-αMePhe-Thr-Ser-Asp-Tyr-Aib-Ile-Aib-Leu-Asp-Lys-Gln-Ala-Gln-Ser-Glu-Phe-Val-Lys-Trp-Leu-Leu-Lys-Gly-Gly-Pro-Ser-Ser-Gly-Ala-Pro-Pro-Pro-Ser-NH$_2$ (SEQ ID NO: 20)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Sieber amide resin (SEQ ID NO: 11) (0.188 meq/g, 53.2 mg) prepared in Reference Example 2 was weighed into a reaction tube, and swollen with DMF. After removal of DMF by filtration, Fmoc-Ser(tBu)-OH (38.3 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 76.8 mg of H-Tyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp(OtBu)-Lys(Boc)-Gln(Trt)-Ala-Gln(Trt)-Ser(tBu)-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)- Sieber amide resin(SEQ ID NO: 46).

To 76.8 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-0DS-P column (250×20 mm I.D.) [Solution A: 0.1% TFA-water, Solution B: 0.1% TFA-containing acetonitrile, flow rate 8 mL/min, A/B: 63/37-53/47 linear concentration gradient elution (60 min)]. The fractions containing the object product were collected and freeze-dried to give 16.6 mg of a white powder.

Mass spectrometry, (M+H)$^+$4169.2 (Calculated: 4169.1)
HPLC elution time: 7.4 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 9

Synthesis of H-Tyr-Aib-Glu-Gly-Thr-αMePhe-Thr-Ser-Asp-Tyr-Aib-Lys-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 21)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, Aib, Lys(Boc), Aib, Tyr(tBu), Asp(OtBu), Ser(tBu), Thr (tBu), αMePhe, Thr(tBu)*, Gly, Glu(OtBu), Aib and Tyr (tBu) (*: overnight reaction). The resin was washed with MeOH, and then dried under reduced pressure to give 72.4 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Lys (Boc)-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser (tBu)-Lys (Boc)-Sieber amide resin(SEQ ID NO: 47).

To 72.4 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-0DS-P column (250×20 mm I.D.) [Solution A: 0.1% TFA-water, Solution B: 0.1% TFA-containing acetonitrile, flow rate 8 mL/min, A/B: 67/33-57/43 linear concentration gradient elution (60 min)]. The fractions containing the object product were collected and freeze-dried to give 13.9 mg of a white powder.

Mass spectrometry, (M+H)$^+$4295.8 (Calculated: 4296.2)
HPLC elution time: 6.9 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 10

Synthesis of H-Tyr-Aib-Glu-Gly-Thr-αMePhe-Thr-Ser-Asp-Tyr-Aib-Ala-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 22)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, Aib, Ala, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 86.1 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Ala-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser(tBu)-Gly-Ala-Pro-Pro-Pro-Ser(tBu)-Lys (Boc)-Sieber amide resin(SEQ ID NO: 48).

To 86.1 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-0DS-P column (250×20 mm I.D.) [Solution A: 0.1% TFA-water, Solution B: 0.1% TFA-containing acetonitrile, flow rate 8 mL/min, A/B: 66/34-56/44 linear concentration gradient elution (60 min)]. The fractions containing the object product were collected and freeze-dried to give 16.2 mg of a white powder.

Mass spectrometry, (M+H)$^+$4238.6 (Calculated: 4239.2)

HPLC elution time: 7.1 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 11

Synthesis of H-Tyr-Aib-Glu-Gly-Thr-αMePhe-Thr-Ser-Asp-Tyr-Aib-Phe-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 23)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, Aib, Phe, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 76.4 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Phe-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser(tBu)-Gly-Ala-Pro-Pro-Pro-Ser(tBu)-Lys (Boc)-Sieber amide resin(SEQ ID NO: 49).

To 76.4 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-0DS-P column (250×20 mm I.D.) [Solution A: 0.1% TFA-water, Solution B: 0.1% TFA-containing acetonitrile, flow rate 8 mL/min, A/B: 65/35-55/45 linear concentration gradient elution (60 min)]. The fractions containing the object product were collected and freeze-dried to give 4.7 mg of a white powder.

Mass spectrometry, (M+H)$^+$4315.1 (Calculated: 4315.2)
HPLC elution time: 7.2 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 12

Synthesis of H-Tyr-Aib-Glu-Gly-Thr-αMePhe-Thr-Ser-Asp-Tyr-Aib-Pya(4)-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH₂ (SEQ ID NO: 24)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, Aib, Pya(4)*, Aib, Tyr(tBu), Asp(OtBu), Ser(tBu), Thr (tBu), αMePhe, Thr(tBu)**, Gly, Glu(OtBu), Aib and Tyr (tBu) (*: 17.4 μL of DIPEA was added during condensation; **: overnight reaction). The resin was washed with MeOH, and then dried under reduced pressure to give 78.4 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Pya (4)-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser(tBu)-Gly-Ala-Pro-Pro-Pro-Ser (tBu)-Lys(Boc)-Sieber amide resin(SEQ ID NO: 50).

To 78.4 mg of the obtained resin was added 1 mL of TFA: m-cresol: thioanisole: ethanedithiol: H₂O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 67/33-57/43 linear concentration gradient elution (60 min)]. The fractions containing the object product were collected and freeze-dried to give 15.2 mg of a white powder.

Mass spectrometry, (M+H)⁺4316.2 (Calculated: 4316.2)
HPLC elution time: 6.9 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 13

Synthesis of H-Tyr-Aib-Glu-Gly-Thr-αMePhe-Thr-Ser-Asp-Tyr-Aib-Ile-αMePhe-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH₂ (SEQ ID NO: 25)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, αMePhe, Ile, Aib, Tyr(tBu), Asp(OtBu), Ser(tBu), Thr (tBu), αMePhe, Thr(tBu)*, Gly, Glu(OtBu), Aib and Tyr (tBu) (*: overnight reaction). The resin was washed with MeOH, and then dried under reduced pressure to give 69.1 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Ile-αMePhe-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser(tBu)-Gly-Ala-Pro-Pro-Pro-Ser (tBu)-Lys(Boc)-Sieber amide resin(SEQ ID NO: 51).

To 69.1 mg of the obtained resin was added 1 mL of TFA: m-cresol: thioanisole: ethanedithiol: H₂O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 64/36-54/46 linear concentration gradient elution (60 min)]. The fractions containing the object product were collected and freeze-dried to give 14.4 mg of a white powder.

Mass spectrometry, (M+H)⁺4356.9 (Calculated: 4357.3)
HPLC elution time: 7.4 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 14

Synthesis of H-Tyr-Aib-Glu-Gly-Thr-αMePhe-Thr-Ser-Asp-Tyr-Aib-Ile-Cha-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 26)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, Cha, Ile, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 71.5 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Ile-Cha-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser(tBu)-Gly-Ala-Pro-Pro-Pro-Ser(tBu)-Lys (Boc)-Sieber amide resin(SEQ ID NO: 52).

To 71.5 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 63/37-53/47 linear concentration gradient elution (60 min)]. The fractions containing the object product were collected and freeze-dried to give 16 mg of a white powder.

Mass spectrometry, (M+H)$^+$4348.7 (Calculated: 4349.3) HPLC elution time: 7.5 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate 3.0 mL/min

Example 15

Synthesis of H-Tyr-Aib-Glu-Gly-Thr-αMePhe-Thr-Ser-Asp-Tyr-Aib-Lys-αMePhe-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 27)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, αMePhe, Lys(Boc), Aib, Tyr(tBu), Asp(OtBu), Ser (tBu), Thr(tBu), αMePhe, Thr(tBu)*, Gly, Glu(OtBu), Aib and Tyr(tBu) (*: overnight reaction). The resin was washed with MeOH, and then dried under reduced pressure to give 77.9 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Lys (Boc)-αMePhe-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser (tBu)-Lys (Boc)-Sieber amide resin (SEQ ID NO: 53).

To 77.9 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 65/35-55/45 linear concentration gradient elution (60 min)]. The fractions containing the object product were collected and freeze-dried to give 13.4 mg of a white powder.

Mass spectrometry, (M+H)$^+$4371.7 (Calculated: 4372.3) HPLC elution time: 7.1 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate 3.0 mL/min

Example 16

Synthesis of H-Tyr-Aib-Glu-Gly-Thr-αMePhe-Thr-Ser-Asp-Tyr-Aib-Lys-Cha-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH₂ (SEQ ID NO: 28)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, Cha, Lys(Boc), Aib, Tyr(tBu), Asp(OtBu), Ser(tBu), Thr(tBu), αMePhe, Thr(tBu)*, Gly, Glu(OtBu), Aib and Tyr (tBu) (*: overnight reaction). The resin was washed with MeOH, and then dried under reduced pressure to give 75.1 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Lys (Boc)-Cha-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser (tBu)-Lys (Boc)-Sieber amide resin(SEQ ID NO: 54).

To 75.1 mg of the obtained resin was added 1 mL of TFA: m-cresol: thioanisole: ethanedithiol: H₂O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 65/35-55/45 linear concentration gradient elution (60 min)]. The fractions containing the object product were collected and freeze-dried to give 14.7 mg of a white powder.

Mass spectrometry, (M+H)⁺4364.7 (Calculated: 4364.3) HPLC elution time: 7.1 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 17

Synthesis of H-Tyr-Aib-Glu-Gly-Thr-αMePhe-Thr-Ser-Asp-Tyr-Aib-Ile-αMeTyr-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH₂ (SEQ ID NO: 29)

H-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin (SEQ ID NO: 12) (0.225 meq/g, 44.4 mg) prepared in Reference Example 3 was weighed into a reaction tube, and swollen with DMF. After removal of DMF by filtration, Fmoc-Gln(Trt)-OH (61.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Lys(Boc), Asp(OtBu), Leu, αMeTyr, Ile, Aib, Tyr(tBu), Asp(OtBu), Ser(tBu), Thr (tBu), αMePhe, Thr(tBu)*, Gly, Glu(OtBu), Aib and Tyr (tBu) (*: overnight reaction). The resin was washed with MeOH, and then dried under reduced pressure to give 56.2 mg of H-Tyr (tBu)-Aib-Glu (OtBu)-Gly-Thr (tBu)-αMePhe-Thr (tBu)-Ser (tBu)-Asp (OtBu)-Tyr (tBu)-Aib-Ile-αMeTyr-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser(tBu)-Gly-Ala-Pro-Pro-Pro-Ser (tBu)-Lys(Boc)-Sieber amide resin(SEQ ID NO: 55).

To 56.2 mg of the obtained resin was added 1 mL of TFA: m-cresol: thioanisole: ethanedithiol: H₂O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 65/35-55/45 linear concentration gradient elution (60 min)]. The fractions containing the object product were collected and freeze-dried to give 1.4 mg of a white powder.

Mass spectrometry, (M+H)⁺4373.8 (Calculated: 4373.2) HPLC elution time: 7.2 min elution condition:

column: Merck Chromolith Performance RP-18e (100×4.6 mm I.D.)

eluent: using Solution A: 0.1% TFA-water, Solution B: 0.1% TFA-containing acetonitrile, A/B: 95/5-35/65 linear concentration gradient elution (10 min)

flow rate: 3.0 mL/min

Example 18

Synthesis of Ac-Tyr-Aib-Glu-Gly-Thr-αMePhe-Thr-Ser-Asp-Tyr-Aib-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 30)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.253 meq/g, 39.5 mg) prepared by an approach similar to Reference Example 1 was weighed into a reaction tube, and swollen with DMF. After removal of DMF by filtration, Fmoc-Ala-OH (31.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). Next, the N-terminal Fmoc group was removed by piperidine treatment, and then DMF (200 μL), DIPEA (17.4 μL) and Ac$_2$O (9.4 μL) were successively added to the resin, and the mixture was shaken for 90 minutes. The reaction solution was filtered off, and the resin was then washed with DMF 6 times. After confirmation of negativity in the Kaiser test, the resin was washed with MeOH, and dried under reduced pressure to give 43 mg of Ac-Tyr(tBu)-Aib-Glu (OtBu)-Gly-Thr (tBu)-αMePhe-Thr (tBu)-Ser (tBu)-Asp (OtBu)-Tyr (tBu)-Aib-Ile-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser (tBu)-Lys(Boc)-Sieber amide resin(SEQ ID NO: 56).

To 43 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 62/38-52/48 linear concentration gradient elution (60 min)]. The fractions containing the object product were collected and freeze-dried to give 7.8 mg of a white powder.

Mass spectrometry, (M+H)$^+$4323.4 (Calculated: 4323.2)
HPLC elution time: 7.5 min
  elution condition:
  column: Merck Chromolith Performance RP-18e (100×4.6 mm I.D.)
  eluent: using Solution A: 0.1% TFA-water, Solution B: 0.1% TFA-containing acetonitrile, A/B: 95/5-35/65 linear concentration gradient elution (10 min)
  flow rate: 3.0 mL/min

Example 19

Synthesis of Benzoyl-Tyr-Aib-Glu-Gly-Thr-αMePhe-Thr-Ser-Asp-Tyr-Aib-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 31)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.253 meq/g, 39.5 mg) prepared in Reference Example 1 was weighed into a reaction tube, and swollen with DMF. After removal of DMF by filtration, Fmoc-Ala-OH (31.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). Next, the N-terminal Fmoc group was removed by piperidine treatment, and then benzoic acid (12.2 mg), 0.5 M Oxymapure in DMF (200 μL) and diisopropylcarbodiimide (15.9 μL) were successively added to the resin, and the mixture was shaken overnight. The reaction solution was filtered off, and the resin was then washed with DMF 6 times. After confirmation of negativity in the Kaiser test, the resin was washed with MeOH, and then dried under reduced pressure to give 54.8 mg of Benzoyl-Tyr(tBu)-Aib-Glu (OtBu)-Gly-Thr (tBu)-αMePhe-Thr (tBu)-Ser (tBu)-Asp (OtBu)-Tyr (tBu)-Aib-Ile-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin(SEQ ID NO: 57).

To 54.8 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 60/40-50/50 linear concentration gradient elution (60 min)]. The fractions containing the object product were collected and freeze-dried to give 10.1 mg of a white powder.

Mass spectrometry, (M+H)$^+$4385.2 (Calculated: 4385.2)
HPLC elution time: 7.7 min
  elution condition:
  column: Merck Chromolith Performance RP-18e (100×4.6 mm I.D.)
  eluent: using Solution A: 0.1% TFA-water, Solution B: 0.1% TFA-containing acetonitrile, A/B: 95/5-35/65 linear concentration gradient elution (10 min)
  flow rate: 3.0 mL/min

Example 20

Synthesis of 4PyCO-Tyr-Aib-Glu-Gly-Thr-αMePhe-Thr-Ser-Asp-Tyr-Aib-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 32)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.253 meq/g, 39.5 mg) prepared in Reference Example 1 was weighed into a reaction tube, and swollen with DMF. After removal of DMF by filtration, Fmoc-Ala-OH (31.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). Next, the N-terminal Fmoc group was removed by piperidine treatment, and then 4-pyridinecarboxilic acid (12.3 mg), 0.5 M Oxymapure in DMF (200 μL) and diisopropylcarbodiimide (15.9 μL) were successively added to the resin, and the mixture was shaken overnight. The reaction solution was filtered off, and the resin was then washed with DMF 6 times. After confirmation of negativity in the Kaiser test, the resin was washed with MeOH, and then dried under reduced pressure to give 62.9 mg of 4PyCO-Tyr(tBu)-Aib-Glu(OtBu)-Gly-Thr(tBu)-αMePhe-Thr(tBu)-Ser(tBu)-Asp(OtBu)-Tyr (tBu)-Aib-Ile-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin(SEQ ID NO: 58).

To 62.9 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-0DS-P column (250×20 mm I.D.) [Solution A: 0.1% TFA-water, Solution B: 0.1% TFA-containing acetonitrile, flow rate 8 mL/min, A/B: 62/38-52/48 linear concentration gradient elution (60 min)]. The fractions containing the object product were collected and freeze-dried to give 13.3 mg of a white powder.

Mass spectrometry, (M+H)$^+$4386.2 (Calculated: 4386.2)
HPLC elution time: 7.3 min
elution condition:
column: Merck Chromolith Performance RP-18e (100×4.6 mm I.D.)
eluent: using Solution A: 0.1% TFA-water, Solution B: 0.1% TFA-containing acetonitrile, A/B: 95/5-35/65 linear concentration gradient elution (10 min)
flow rate: 3.0 mL/min

Example 21

Synthesis of cPrCO-Tyr-Aib-Glu-Gly-Thr-αMePhe-Thr-Ser-Asp-Tyr-Aib-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 33)

H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.253 meq/g, 39.5 mg) prepared in Reference Example 1 was weighed into a reaction tube, and swollen with DMF. After removal of DMF by filtration, Fmoc-Ala-OH (31.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr(tBu)*, Gly, Glu(OtBu), Aib and Tyr(tBu) (*: overnight reaction). Next, the N-terminal Fmoc group was removed by piperidine treatment, and then cyclopropanecarboxylic acid (8.6 mg), 0.5 M Oxymapure in DMF (200 μL) and diisopropylcarbodiimide (15.9 μL) were successively added to the resin, and the mixture was shaken overnight. The reaction solution was filtered off, and the resin was then washed with DMF 6 times. After confirmation of negativity in the Kaiser test, the resin was washed with MeOH, and then dried under reduced pressure to give 61.8 mg of cPrCO-Tyr(tBu)-Aib-Glu(OtBu)-Gly-Thr(tBu)-αMePhe-Thr(tBu)-Ser(tBu)-Asp(OtBu)-Tyr (tBu)-Aib-Ile-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser (tBu)-Gly-Ala-Pro-Pro-Pro-Ser(tBu)-Lys(Boc)-Sieber amide resin(SEQ ID NO: 59).

To 61.8 mg of the obtained resin was added 1 mL of TFA: m-cresol: thioanisole: ethanedithiol: H$_2$O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-0DS-P column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 11.7 mg of a white powder.

Mass spectrometry, (M+H)$^+$4349.2 (Calculated: 4349.2)
HPLC elution time: 7.6 min
elution condition:
column: Merck Chromolith Performance RP-18e (100×4.6 mm I.D.)

Example 22

Synthesis of amidino-Tyr-Aib-Glu-Gly-Thr-αMe-
Phe-Thr-Ser-Asp-Tyr-Aib-Ile-Aib-Leu-Asp-Lys-
Gln-Ala-Gln-Ala-Glu-Phe-Val-Lys-Trp-Leu-Leu-
Lys-Gly-Gly-Pro-Ser-Ser-Gly-Ala-Pro-Pro-Pro-Ser-
Lys-NH₂ (SEQ ID NO: 34)

H-Glu(OtBu)-Phe-Val-Lys(Boc)-Trp(Boc)-Leu-Leu-Lys (Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.253 meq/g, 39.5 mg) prepared in Reference Example 1 was weighed into a reaction tube, and swollen with DMF. After removal of DMF by filtration, Fmoc-Ala-OH (31.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr (tBu)*, Gly, Glu(OtBu), Aib and Tyr(tBu) (*: overnight reaction). Next, the N-terminal Fmoc group was removed by piperidine treatment, and then DMF (200 μL), N,N'-Bis(tert-butoxycarbonyl)-1H-pyrazolo-1-carboxamidine (31 mg) and DIPEA (17.4 μL) were successively added to the resin, and the mixture was shaken overnight. The reaction solution was filtered off, and then DMF (200 μL), N,N'-Bis(tert-butoxycarbonyl)-1H-pyrazolo-1-carboxamidine (31 mg) and DIPEA (17.4 μL) were successively added to the resin, and the mixture was shaken overnight again. The reaction solution was filtered off, and the resin was then washed with DMF 6 times. After confirmation of negativity in the Kaiser test, the resin was washed with MeOH, and then dried under reduced pressure to give 54.7 mg of BocNHC(=NBoc)-Tyr(tBu)-Aib-Glu(OtBu)-Gly-Thr(tBu)-αMePhe-Thr(tBu)-Ser (tBu)-Asp (OtBu)-Tyr (tBu)-Aib-Ile-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser (tBu)-Ser(tBu)-Gly-Ala-Pro-Pro-Pro-Ser(tBu)-Lys(Boc)-Sieber amide resin(SEQ ID NO: 60).

To 54.7 mg of the obtained resin was added 1 mL of TFA: m-cresol: thioanisole: ethanedithiol: H₂O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 62/38-52/48 linear concentration gradient elution (60 min)]. The fractions containing the object product were collected and freeze-dried to give 10.7 mg of a white powder.

Mass spectrometry, (M+H)⁺4323.2 (Calculated: 4323.2)
HPLC elution time: 7.3 min
elution condition:
column: Merck Chromolith Performance RP-18e (100×4.6 mm I.D.)
eluent: using Solution A: 0.1% TFA-water, Solution B: 0.1% TFA-containing acetonitrile, A/B: 95/5-35/65 linear concentration gradient elution (10 min)
flow rate: 3.0 mL/min Example 23

Synthesis of H-NMeTyr-Aib-Glu-Gly-Thr-αMePhe-
Thr-Ser-Asp-Tyr-Aib-Ile-Aib-Leu-Asp-Lys-Gln-Ala-
Gln-Ala-Glu-Phe-Val-Lys-Trp-Leu-Leu-Lys-Gly-
Gly-Pro-Ser-Ser-Gly-Ala-Pro-Pro-Pro-Ser-Lys-NH₂
(SEQ ID NO: 35)

H-Glu(OtBu)-Phe-Val-Lys(Boc)-Trp(Boc)-Leu-Leu-Lys (Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.253 meq/g, 39.5 mg) prepared in Reference Example 1 was weighed into a reaction tube, and swollen with DMF. After removal of DMF by filtration, Fmoc-Ala-OH (31.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Aib, Ile*, Aib, Tyr(tBu), Asp(OtBu), Ser(tBu), Thr(tBu), αMePhe, Thr (tBu)*, Gly, Glu(OtBu), Aib and NMeTyr(tBu) (*: overnight reaction). The resin was washed with MeOH, and then dried under reduced pressure to give 66.2 mg of H-NMeTyr(tBu)-Aib-Glu(OtBu)-Gly-Thr(tBu)-αMePhe-Thr(tBu)-Ser(tBu)-Asp(OtBu)-Tyr(tBu)-Aib-Ile-Aib-Leu-Asp (OtBu)-Lys (Boc)-Gln (Trt)-Ala-Gln (Trt)-Ala-Glu (OtBu)-Phe-Val-Lys (Boc)-Trp (Boc)-Leu-Leu-Lys (Boc)-Gly-Gly-Pro-Ser(tBu)-Ser(tBu)-Gly-Ala-Pro-Pro-Pro-Ser(tBu)-Lys(Boc)-Sieber amide resin(SEQ ID NO: 61).

To 66.2 mg of the obtained resin was added 1 mL of TFA: m-cresol: thioanisole: ethanedithiol: H₂O: triisopropylsilane (80:5:5:5:2.5:2.5), and the mixture was stirred for 1.5 hours. Diethyl ether was added to the reaction solution to obtain precipitation, and the precipitation was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 63/37-53/47 linear concentration gradient elution (60 min)]. The fractions containing the object product were collected and freeze-dried to give 9 mg of a white powder.

Mass spectrometry, (M+H)⁺4295.1 (Calculated: 4295.2)
HPLC elution time: 7.2 min elution condition:
column: Merck Chromolith Performance RP-18e (100×4.6 mm I.D.)
eluent: using Solution A: 0.1% TFA-water, Solution B: 0.1% TFA-containing acetonitrile, A/B: 95/5-35/65 linear concentration gradient elution (10 min)
flow rate: 3.0 mL/min Example 24

Synthesis of H-Tyr-Aib-Glu-Gly-Thr-αMePhe-Thr-Ser-Asp-Tyr-Aib-Lys-Tyr-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 36)

The H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.244 meq/g, 41.0 mg) prepared in Reference Example 1 was weighed into a reaction tube, and swollen with DMF. After removal of DMF by filtration, Fmoc-Ala-OH (31.1 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Tyr(tBu), Lys(Boc)*, Aib, Tyr(tBu), Asp(OtBu), Ser(tBu), Thr(tBu), αMePhe, Thr(tBu)*, Gly, Glu(OtBu), Aib and Tyr (tBu) (*: overnight reaction). The resin was washed with MeOH, and then dried under reduced pressure to give 66.8 mg of H-Tyr(tBu)-Aib-Glu(OtBu)-Gly-Thr(tBu)-αMePhe-Thr(tBu)-Ser(tBu)-Asp(OtBu)-Tyr(tBu)-Aib-Lys(Boc)-Tyr(tBu)-Leu-Asp(OtBu)-Lys(Boc)-Gln(Trt)-Ala-Gln(Trt)-Ala-Glu(OtBu)-Phe-Val-Lys(Boc)- Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin(SEQ ID NO: 62).
To 66.8 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitate, and the precipitate was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 66/34-56/44 linear concentration gradient elution (60 min)]. The fractions containing the object product were collected and freeze-dried to give 16.1 mg of a white powder.
Mass spectrometry, (M+H)$^+$4374.6 (Calculated: 4374.2)
HPLC elution time: 6.9 min
elution condition:
column: Merck Chromolith Performance RP-18e (100×4.6 mm I.D.)
eluent: using Solution A: 0.1% TFA-water, Solution B: 0.1% TFA-containing acetonitrile, A/B: 95/5-35/65 linear concentration gradient elution (10 min)
flow rate: 3.0 mL/min Example 25

Synthesis of H-Tyr-Aib-Glu-Gly-Thr-αMePhe-Thr-Ser-Asp-Tyr-Aib-Lys-Tyr-Leu-Asp-Lys-Gln-Ala-Gln-Gln-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 37)

The H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 10) (0.244 meq/g, 41.0 mg) prepared in Reference Example 1 was weighed into a reaction tube, and swollen with DMF. After removal of DMF by filtration, Fmoc-Gln(Trt)-OH (61.1 mg), 0.5 M Oxymapure in DMF (200 µL) and diisopropylcarbodiimide (15.9 µL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Tyr(tBu), Lys(Boc)*, Aib, Tyr(tBu), Asp(OtBu), Ser(tBu), Thr(tBu), αMePhe, Thr(tBu)*, Gly, Glu(OtBu), Aib and Tyr (tBu) (*: overnight reaction). The resin was washed with MeOH, and then dried under reduced pressure to give 55.0 mg of H-Tyr(tBu)-Aib-Glu(OtBu)-Gly-Thr (tBu)-αMePhe-Thr (tBu)-Ser (tBu)-Asp (OtBu)-Tyr (tBu)-Aib-Lys (Boc)-Tyr (tBu)-Leu-Asp (OtBu)-Lys (Boc)-Gln (Trt)-Ala-Gln (Trt)-Gln (Trt)-Glu (OtBu)-Phe-Val-Lys (Boc)-Trp (Boc)-Leu-Leu-Lys(Boc)-Gly-Gly-Pro-Ser(tBu)-Ser(tBu)-Gly-Ala-Pro-Pro-Pro-Ser(tBu)-Lys(Boc)-Sieber amide resin (SEQ ID NO: 63).
To 55.0 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitate, and the precipitate was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 66/34-56/44 linear concentration gradient elution (60 min)]. The fractions containing the object product were collected and freeze-dried to give 13.7 mg of a white powder.
Mass spectrometry, (M+H)$^+$4431.5 (Calculated: 4431.3)
HPLC elution time: 6.9 min
elution condition:
column: Merck Chromolith Performance RP-18e (100×4.6 mm I.D.)
eluent: using Solution A: 0.1% TFA-water, Solution B: 0.1% TFA-containing acetonitrile, A/B: 95/5-35/65 linear concentration gradient elution (10 min)
flow rate: 3.0 mL/min

Example 26

Synthesis of H-Tyr-Aib-Glu-Gly-Thr-αMePhe-Thr-Ser-Asp-Tyr-Aib-Lys-Tyr-Leu-Asp-Lys-Gln-Ala-Gln-Gln-Glu-Phe-Val-Lys-Trp-Leu-Leu-Lys-Gly-Gly-Pro-Ser-Ser-Gly-Ala-Pro-Pro-Pro-Ser-NH$_2$ (SEQ ID NO: 38)

The H-Glu(OtBu)-Phe-Val-Lys(Boc)-Trp(Boc)-Leu-Leu-Lys(Boc)-Gly-Gly-Pro-Ser(tBu)-Ser(tBu)-Gly-Ala-Pro-Pro-Pro-Ser(tBu)-Sieber amide resin (SEQ ID NO: 11) (0.188 meq/g, 53.2 mg) prepared in Reference Example 2 was weighed into a reaction tube, and swollen with DMF. After removal of DMF by filtration, Fmoc-Gln(Trt)-OH (61.1 mg), 0.5 M Oxymapure in DMF (200 μL) and diisopropylcarbodiimide (15.9 μL) were successively added to the resin, and then the mixture was shaken for 1.5 hours. The reaction solution was filtered off, and the resin was then washed with DMF 6 times. After confirmation of negativity in the Kaiser test, a DMF solution of 20% piperidine was added thereto, and the mixture was shaken for 1 minute. The solution was filtered off, and a DMF solution of 20% piperidine was then added thereto again, and the mixture was shaken for 20 minutes. The solution was filtered off, and the resin was then washed with DMF 10 times. This Fmoc amino acid condensation-Fmoc deprotection cycle was repeated to successively condense Gln(Trt), Ala, Gln(Trt), Lys(Boc), Asp(OtBu), Leu, Tyr(tBu), Lys(Boc)*, Aib, Tyr(tBu), Asp(OtBu), Ser(tBu), Thr(tBu), αMePhe, Thr(tBu)*, Gly, Glu(OtBu), Aib and Tyr (tBu) (*: overnight reaction). The resin was washed with MeOH, and then dried under reduced pressure to give 95.4 mg of H-Tyr(tBu)-Aib-Glu(OtBu)-Gly-Thr (tBu)-αMePhe-Thr (tBu)-Ser (tBu)-Asp (OtBu)-Tyr (tBu)-Aib-Lys (Boc)-Tyr (tBu)-Leu-Asp (OtBu)-Lys (Boc)-Gln (Trt)-Ala-Gln (Trt)-Gln (Trt)-Glu (OtBu)-Phe-Val-Lys (Boc)-Trp (Boc)-Leu-Leu-Lys(Boc)-Gly-Gly-Pro-Ser(tBu)-Ser(tBu)-Gly-Ala-Pro-Pro-Pro-Ser(tBu)-Sieber amide resin(SEQ ID NO: 64).

To 95.4 mg of the obtained resin was added 1 mL of TFA:m-cresol:thioanisole:ethanedithiol:H$_2$O:triisopropylsilane (80:5:5:5:2.5:2.5), and the mixture was stirred for 1.5 hours. Diethyl ether was added to the reaction solution to obtain precipitate, and the precipitate was washed by repeating three times an operation to remove the supernatant after centrifugation. The residue was extracted with 50% aqueous acetic acid solution, and the resin was removed by filtration, followed by preparative HPLC using Daisopak SP-100-5-ODS-P column (250×20 mm I.D.) [Solution A: 0.1% TFA-water, Solution B: 0.1% TFA-containing acetonitrile, flow rate 8 mL/min, A/B: 61/39-51/49 linear concentration gradient elution (60 min)]. The fractions containing the object product were collected and freeze-dried to give 20.0 mg of a white powder.

Mass spectrometry, (M+H)$^+$4303.0 (Calculated: 4303.2)
HPLC elution time: 7.1 min
  elution condition:
  column: Merck Chromolith Performance RP-18e (100×4.6 mm I.D.)
  eluent: using Solution A: 0.1% TFA-water, Solution B: 0.1% TFA-containing acetonitrile, A/B: 95/5-35/65 linear concentration gradient elution (10 min)
  flow rate: 3.0 mL/min

Test Example 1

Evaluation of agonist activity against human GIPR, human GLP-1R and human glucagon R using rise in intracellular cAMP concentration as index (1) Construction of Expression Plasmid for the Human GIPR Gene The human GIPR gene having a sequence identical to the sequence of GenBank Accession No. U39231 was cloned into pMSRα-neo vector to prepare hGIPR/pMSRα-neo.

(2) Construction of Reporter Plasmid-Expressing Cell

The luciferase reporter gene having an upstream cAMP response sequence was introduced to CHO-K1 cells to construct CRE-LUC/CHO-K1 cells.

(3) Construction of Reporter Plasmid

Four copies of the cAMP response sequence and the Zeocin resistance gene were introduced to pGL3(R2.2)-Basic Vector (Promega) to construct Cre-luc(Zeo) reporter plasmid.

(4) Introduction of the Human GIPR Gene into CRE-LUC/CHO-K1 Cell and Obtainment of Expressing Cell The plasmid hGIPR/pMSRα-neo obtained in (1) was introduced to the CRE-LUC/CHO-K1 cells obtained in (2) to obtain transformants. Next, a cell line induced to express luciferase, i.e., hGIPR/CRE-LUC/CHO-K1 cells, were selected from the obtained transformants by the addition of GIP.

(5) Construction of Expression Plasmid for the Human GLP-1R Gene

The human GLP-1R gene having a sequence identical to the sequence of GenBank Accession No. NM_002062 was cloned into pIRESneo3 vector to prepare hGLP-1/pIRESneo3.

(6) Introduction of the Human GLP-1R Gene and the Reporter Plasmid into CHO-K1 Cell and Obtainment of Expressing Cell The Cre-luc(Zeo) obtained in (3) and the plasmid hGLP-1/pIRESneo3 obtained in (5) were introduced to CHO-K1 cells to obtain transformants. Next, a cell line induced to express luciferase, i.e., hGLP-1R/CRE-luc/CHO-K1 cells, were selected from the obtained transformants by the addition of GLP-1.

(7) Construction of Expression Plasmid for the Human Glucagon R Gene

The human glucagon R gene having a sequence identical to the sequence of GenBank Accession No. NM_000160 was cloned into pMSRα-neo vector to prepare hGlucagonR/pMSRα-neo.

(8) Introduction of the Human Glucagon R Gene into CRE-LUC/CHO-K1 Cell and Obtainment of Expressing Cell The plasmid hGlucagonR/pMSRα-neo obtained in (7) was introduced to the CRE-LUC/CHO-K1 cells obtained in (2) to obtain transformants. Next, a cell line induced to express luciferase, i.e., hGlucagonR/CRE-LUC/CHO-K1 cells, were selected from the obtained transformants by the addition of glucagon.

(9) Reporter Assay

The hGIPR/CRE-LUC/CHO-K1 cells were inoculated at a cell density of 25 μL/well (5×10$^4$ cells/well) to a 384-well white plate (Corning), and cultured overnight in Ham F12 medium containing 10% fetal bovine serum, 100 U/mL penicillin and 100 μg/mL streptomycin in a CO$_2$ incubator of 37° C. A medium containing a test compound was added at a concentration of 5 μL/well to the cells, and the resultant cells were incubated for 4 hours in a CO$_2$ incubator of 37° C. to give the final concentration of 1 μM. PicaGene LT7.5 (Toyo Ink Co., Ltd.) was added thereto at a concentration of 30 μL/well, and the mixture was shaken with light shielded. After 30 minutes, the luciferase activity was measured using a plate reader Envision (PerkinElmer). The luciferase activity in the presence of 10 nM GIP was defined as 100%, and the luciferase activity from the addition of DMSO instead of the test compound was defined as 0%. The GIPR agonist activity was calculated with a rise in intracellular cAMP concentration as an index. The results are shown in Table 2.

The GLP-1R agonist activity was assayed in the same way as above using the hGLP-1R/CRE-luc/CHO-K1 cells. The luciferase activity in the presence of 10 nM GLP-1 was defined as 100%, and the luciferase activity from the addition of DMSO instead of the test compound was defined as 0%. The GLP-1R agonist activity was calculated with a rise in intracellular cAMP concentration as an index. The results are shown in Table 2.

The glucagon R agonist activity was assayed in the same way as above using the hGlucagonR/CRE-LUC/CHO-K1 cells. The luciferase activity in the presence of 10 nM glucagon was defined as 100%, and the luciferase activity from the addition of DMSO instead of the test compound was defined as 0%. The glucagon agonist activity was calculated with a rise in intracellular cAMP concentration as an index. The results are shown in Table 2.

As shown in Table 2, the compound of the present invention has a superior activating action on GLP-1 receptors and GIP receptors. In addition, the compound of the present invention has a low glucagon receptor-activating action.

TABLE 2

| Example | Agonist activity ($EC_{50}$) | | |
|---|---|---|---|
| | hGIPR | hGLP-1R | hGCGR |
| 1 | 8.1E−12 | 1.2E−11 | >1.0E−06 |
| 2 | 6.8E−12 | 1.6E−11 | >1.0E−06 |
| 3 | 7.1E−12 | 1.3E−11 | >1.0E−06 |
| 4 | 4.9E−12 | 9.9E−12 | >1.0E−06 |
| 5 | 5.5E−12 | 7.2E−12 | >1.0E−06 |
| 6 | 7.3E−12 | 1.6E−11 | >1.0E−06 |
| 7 | 6.9E−12 | 8.8E−12 | >1.0E−06 |
| 8 | 8.0E−12 | 1.4E−11 | >1.0E−06 |
| 9 | 8.0E−12 | 1.5E−11 | >1.0E−06 |
| 10 | 5.4E−12 | 8.3E−12 | >1.0E−06 |
| 11 | 1.5E−11 | 2.2E−11 | >1.0E−06 |
| 12 | 7.2E−12 | 1.4E−11 | >1.0E−06 |
| 13 | 7.2E−12 | 1.1E−11 | >1.0E−06 |
| 14 | 1.3E−11 | 2.1E−11 | >1.0E−06 |
| 15 | 1.3E−11 | 1.5E−11 | >1.0E−06 |
| 16 | 9.1E−12 | 1.5E−11 | >1.0E−06 |
| 17 | 1.4E−11 | 1.8E−11 | >1.0E−06 |
| 18 | 2.7E−11 | 1.3E−10 | >1.0E−06 |
| 19 | 2.4E−11 | 3.7E−11 | >1.0E−06 |
| 20 | 2.6E−11 | 1.3E−10 | >1.0E−06 |
| 21 | 2.4E−11 | 5.5E−11 | >1.0E−06 |
| 22 | 1.9E−11 | 3.5E−11 | >1.0E−06 |
| 23 | 1.6E−11 | 1.6E−11 | >1.6E−11 |
| 24 | 9.9E−12 | 1.1E−11 | >1.0E−06 |
| 25 | 1.3E−11 | 1.4E−11 | >1.0E−06 |
| 26 | 1.3E−11 | 1.5E−11 | >1.0E−06 |

Test Example 2

2-Days Continuous Subcutaneous Administration Test

The feeding suppressive activity of a test compound was examined by the method described below.

The test compound was dissolved in a solvent (50% DMSO) so that sustained release would occur at 10 nmol/kg/day, and the solution was filled in the Alzet Pump (DURECT Corporation, model: 1003D). The pump thus filled with the solution to be administered was immersed in physiological saline for priming, and then used. The pump was embedded by the following method. Each male C57BL/6J mouse at 8-9 weeks of age (20-26° C., allowed to take food and water ad libitum; 12-hour bright-12-hour dark cycle) was anesthetized; the skin in the upper back thereof was incised, and the above-mentioned pump was embedded subcutaneously; the incision was sutured. After weighing, this mouse was returned to the rearing cage (reared alone), and given previously weighed food; food consumption as of 2 days after the start of administration was measured. The food consumption was calculated by subtracting the amount of remaining food from the weight of the food given on the day of the start of administration. When the food consumption of a control group receiving administration of the solvent alone was regarded as a suppression rate of 0%, the feeding suppressive activity of each test compound was evaluated on the basis of 2-days cumulative food consumption after the start of administration. The food intake suppression rate (%) of the test compound was defined as (Food consumption of the control group−Food consumption of the test compound-administered group)/Food consumption of the control group×100.

As shown in Table 3, the compound of the present invention has a superior food intake suppressive action.

TABLE 3

| Example | Food intake suppression (%) |
|---|---|
| 1 | 42.68 |
| 2 | 64.80 |
| 3 | 46.49 |
| 4 | 57.01 |
| 5 | 60.99 |
| 6 | 65.20 |
| 8 | 48.34 |
| 9 | 45.23 |
| 10 | 62.04 |
| 11 | 49.99 |
| 12 | 55.07 |
| 13 | 57.12 |
| 14 | 47.47 |
| 15 | 58.80 |
| 16 | 54.24 |
| 17 | 55.42 |
| 19 | 34.79 |
| 22 | 35.51 |
| 23 | 52.62 |
| 24 | 54.18 |
| 25 | 53.12 |
| 26 | 53.06 |

Test Example 3

2-Weeks Continuous Subcutaneous Administration Study in DIO Mice

The anti-obesity activity of a test compound was examined by the method described below.

Diet-induced obesity (DIO) mice were prepared by feeding male C57BL/6J mice with high-fat diet (D12451: Research Diets, Inc.). The test compound was dissolved in a solvent (50% DMSO) so that sustained release would occur at 1 nmol/kg/day, and the solution was filled in the Alzet Pump (DURECT Corporation, model: 1002). The pump thus filled with the solution to be administered was immersed in physiological saline for priming, and then used. The pump was embedded by the following method. Each male DIO-057BL/6J mouse at 35-37 weeks of age (20-26° C., allowed to take food and water ad libitum; 12-hour bright-12-hour dark cycle) was anesthetized; the skin in the upper back thereof was incised, and the above-mentioned pump was embedded subcutaneously; the incision was sutured. After weighing, this mouse was returned to the rearing cage (reared alone), and given previously weighed food; the body weight was measured every 1 to 3 days after the start of administration. The anti-obesity activity of each test compound was evaluated on the basis of the rate of weight loss 2 weeks after the start of administration, with the rate of weight loss in a control group receiving administration of the solvent alone regarded as 0%.

As shown in Table 4, the compound of the present invention has a superior anti-obesity activity.

TABLE 4

| Example | Change in body weight |
|---------|----------------------|
| 2 | −16.3 |
| 24 | −11.1 |
| 25 | −11.2 |
| 26 | −16.2 |

Test Example 4

Solubility Test

The solubility of a test compound was examined by the method described below.

The test compound of approximately 2 mg was measured precisely. Solvents (10 µL, 20 µL or 40 µL) with different pH (Britton-Robinson buffer (pH 3, 5, 7, 9)) were added to each test compound at 25° C., and the solubility was observed visually.

As shown in Table 5, all the test compounds showed good solubility at each pH.

TABLE 5

| | Solubility (mg /mL) | | | |
|---------|------|------|------|------|
| Example | pH 3 | pH 5 | pH 7 | pH 9 |
| 2 | >100 | >100 | >50 | >50 |
| 24 | >200 | >200 | >200 | >200 |
| 25 | >200 | >200 | >200 | >200 |
| 26 | >200 | >200 | >200 | >200 |

Formulation Example 1

| (1) | Compound of Example 1 | 10.0 mg |
|-----|----------------------|---------|
| (2) | Lactose | 70.0 mg |
| (3) | Cornstarch | 50.0 mg |
| (4) | Soluble starch | 7.0 mg |
| (5) | Magnesium stearate | 3.0 mg |

Compound of Example 1 (10.0 mg) and magnesium stearate (3.0 mg) are granulated with an aqueous soluble starch solution (0.07 ml) (7.0 mg as soluble starch), dried and mixed with lactose (70.0 mg) and cornstarch (50.0 mg). The mixture is compressed to give a tablet.

Formulation Example 2

| (1) | Compound of Example 1 | 5.0 mg |
|-----|----------------------|--------|
| (2) | Sodium chloride | 20.0 mg |
| (3) | Distilled water | to total amount 2 ml |

Compound of Example 1 (5.0 mg) and sodium chloride (20.0 mg) are dissolved in distilled water, and water is added to a total amount of 2.0 ml. The solution is filtered, and filled in a 2 ml ampoule under aseptic conditions. The ampoule is sterilized and tightly sealed to give a solution for injection.

INDUSTRIAL APPLICABILITY

The compound of the present invention has superior GLP-1 receptor/GIP receptor coagonist activity, and is useful as a drug for the prophylaxis or treatment of various diseases associated with GLP-1 receptor/GIP receptor, for example, obesity.

All the publications, patents, and the patent applications cited herein are incorporated herein by reference in their entireties.

FREE TEXT FOR SEQUENCE LISTING

SEQ ID NO: 1: Artificial sequence (synthetic peptide (formula (I)))
SEQ ID NO: 2: Artificial sequence (Synthetic peptide (C-terminal sequence))
SEQ ID NO: 3: Artificial sequence (Synthetic peptide (C-terminal sequence))
SEQ ID NO: 4: Artificial sequence (Synthetic peptide (C-terminal sequence))
SEQ ID NO: 5: Artificial sequence (Synthetic peptide (C-terminal sequence))
SEQ ID NO: 6: Artificial sequence (Synthetic peptide (C-terminal sequence))
SEQ ID NO: 7: Artificial sequence (Synthetic peptide (C-terminal sequence))
SEQ ID NO: 8: Artificial sequence (Synthetic peptide (C-terminal sequence))
SEQ ID NO: 9: Artificial sequence (Synthetic peptide (C-terminal sequence))
SEQ ID NO: 10: Artificial sequence (Synthetic peptide Reference Example 1
SEQ ID NO: 11: Artificial sequence (Synthetic peptide Reference Example 2
SEQ ID NO: 12: Artificial sequence (Synthetic peptide Reference Example 3
SEQ ID NO: 13: Artificial sequence (Synthetic peptide (Example 1))
SEQ ID NO: 14: Artificial sequence (Synthetic peptide (Example 2))
SEQ ID NO: 15: Artificial sequence (Synthetic peptide (Example 3))
SEQ ID NO: 16: Artificial sequence (Synthetic peptide (Example 4))
SEQ ID NO: 17: Artificial sequence (Synthetic peptide (Example 5))
SEQ ID NO: 18: Artificial sequence (Synthetic peptide (Example 6))
SEQ ID NO: 19: Artificial sequence (Synthetic peptide (Example 7))
SEQ ID NO: 20: Artificial sequence (Synthetic peptide (Example 8))
SEQ ID NO: 21: Artificial sequence (Synthetic peptide (Example 9))
SEQ ID NO: 22: Artificial sequence (Synthetic peptide (Example 10))
SEQ ID NO: 23: Artificial sequence (Synthetic peptide (Example 11))
SEQ ID NO: 24: Artificial sequence (Synthetic peptide Example 12

SEQ ID NO: 25: Artificial sequence (Synthetic peptide (Example 13))
SEQ ID NO: 26: Artificial sequence (Synthetic peptide (Example 14))
SEQ ID NO: 27: Artificial sequence (Synthetic peptide (Example 15))
SEQ ID NO: 28: Artificial sequence (Synthetic peptide (Example 16))
SEQ ID NO: 29: Artificial sequence (Synthetic peptide (Example 17))
SEQ ID NO: 30: Artificial sequence (Synthetic peptide (Example 18))
SEQ ID NO: 31: Artificial sequence (Synthetic peptide (Example 19))
SEQ ID NO: 32: Artificial sequence (Synthetic peptide (Example 20))
SEQ ID NO: 33: Artificial sequence (Synthetic peptide (Example 21))
SEQ ID NO: 34: Artificial sequence (Synthetic peptide (Example 22))
SEQ ID NO: 35: Artificial sequence (Synthetic peptide (Example 23))
SEQ ID NO: 36: Artificial sequence (Synthetic peptide (Example 24))
SEQ ID NO: 37: Artificial sequence (Synthetic peptide Example 25
SEQ ID NO: 38: Artificial sequence (Synthetic peptide Example 26

The invention claimed is:

1. A peptide consisting of the amino acid sequence H-Tyr-Aib-Glu-Gly-Thr-Phe-Thr-Ser-Asp-Tyr-Aib-Lys-Tyr-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO:36) or a salt thereof.

2. A peptide consisting of the amino acid sequence H-Tyr-Aib-Glu-Gly-Thr-Phe-Thr-Ser-Asp-Tyr-Aib-Ile-Aib-Leu-Asp-Lys-Gln-Ala-Gln-Ala-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO: 14) or a salt thereof.

3. A peptide consisting of the amino acid sequence H-Tyr-Aib-Glu-Gly-Thr-Phe-Thr-Ser-Asp-Tyr-Aib-Lys-Tyr-Leu-Asp-Lys-Gln-Ala-Gln-Gln-Glu-Phe-Val-Lys-Trp-Leu-Leu-Lys-Gly-Gly-Pro-Ser-Ser-Gly-Ala-Pro-Pro-Pro-Ser-Lys-NH$_2$ (SEQ ID NO:37) or a salt thereof.

4. A peptide consisting of the amino acid sequence H-Tyr-Aib-Glu-Gly-Thr-αMePhe-Thr-Ser-Asp-Tyr-Aib-Lys-Tyr-Leu-Asp-Lys-Gln-Ala-Gln-Gln-Glu-Phe-Val-Lys-Trp-Leu-Leu-Lys-Gly-Gly-Pro-Ser-Ser-Gly-Ala-Pro-Pro-Pro-Ser-NH$_2$ (SEQ ID NO: 38) or a salt thereof.

* * * * *

```
                      SEQUENCE LISTING

<160> NUMBER OF SEQ ID NOS: 64

<210> SEQ ID NO 1
<211> LENGTH: 29
<212> TYPE: PRT
<213> ORGANISM: Artificial Sequence
<220> FEATURE:
<223> OTHER INFORMATION: Synthetic Peptide (Formula (I))
<220> FEATURE:
<221> NAME/KEY: MOD_RES
<222> LOCATION: (1)..(1)
<223> OTHER INFORMATION: N terminal P1 group
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib or Ala
<220> FEATURE:
<221> NAME/KEY: misc_feature
<222> LOCATION: (12)..(12)
<223> OTHER INFORMATION: Xaa stands for Ala, Ile, Lys, Phe or Pya(4)
<220> FEATURE:
<221> NAME/KEY: misc_feature
<222> LOCATION: (13)..(13)
<223> OTHER INFORMATION: Xaa stands for Aib, Cha, Leu, alpha-MePhe, or
      alpha-MeTyr
<220> FEATURE:
<221> NAME/KEY: misc_feature
<222> LOCATION: (16)..(16)
<223> OTHER INFORMATION: Xaa stands for Lys or Ser
<220> FEATURE:
<221> NAME/KEY: misc_feature
<222> LOCATION: (17)..(17)
<223> OTHER INFORMATION: Xaa stands for Gln or Ile
<220> FEATURE:
<221> NAME/KEY: misc_feature
<222> LOCATION: (20)..(20)
<223> OTHER INFORMATION: Xaa stands for Ala or Ser
<220> FEATURE:
<221> NAME/KEY: misc_feature
<222> LOCATION: (29)..(29)
<223> OTHER INFORMATION: Xaa stands for Gln or Gly
<220> FEATURE:
<221> NAME/KEY: NON_TER
<222> LOCATION: (29)..(29)

<400> SEQUENCE: 1

Tyr Xaa Glu Gly Thr Phe Thr Ser Asp Tyr Xaa Xaa Xaa Leu Asp Xaa
1               5                   10                  15

Xaa Ala Gln Xaa Glu Phe Val Lys Trp Leu Leu Lys Xaa
            20                  25
```

```
<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide (C-terminal sequence)
<220> FEATURE:
<221> NAME/KEY: NON_TER
<222> LOCATION: (1)..(1)

<400> SEQUENCE: 2

Gly Pro Ser Ser Gly Ala Pro Pro Pro Ser Lys
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide (C-terminal sequence)
<220> FEATURE:
<221> NAME/KEY: NON_TER
<222> LOCATION: (1)..(1)

<400> SEQUENCE: 3

Gly Pro Ser Ser
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide (C-terminal sequence)
<220> FEATURE:
<221> NAME/KEY: NON_TER
<222> LOCATION: (1)..(1)

<400> SEQUENCE: 4

Gly Pro Ser Ser Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide (C-terminal sequence)
<220> FEATURE:
<221> NAME/KEY: NON_TER
<222> LOCATION: (1)..(1)

<400> SEQUENCE: 5

Gly Pro Ser Ser Gly Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide (C-terminal sequence)
<220> FEATURE:
<221> NAME/KEY: NON_TER
<222> LOCATION: (1)..(1)

<400> SEQUENCE: 6

Gly Pro Ser Ser Gly Ala Pro
```

```
<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide (C-terminal sequence)
<220> FEATURE:
<221> NAME/KEY: NON_TER
<222> LOCATION: (1)..(1)

<400> SEQUENCE: 7

Gly Pro Ser Ser Gly Ala Pro Pro
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide (C-terminal sequence)
<220> FEATURE:
<221> NAME/KEY: NON_TER
<222> LOCATION: (1)..(1)

<400> SEQUENCE: 8

Gly Pro Ser Ser Gly Ala Pro Pro Pro
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic Peptide (C-terminal sequence)
<220> FEATURE:
<221> NAME/KEY: NON_TER
<222> LOCATION: (1)..(1)

<400> SEQUENCE: 9

Gly Pro Ser Ser Gly Ala Pro Pro Pro Ser
1               5                   10

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide (Reference Example 1)
<220> FEATURE:
<221> NAME/KEY: MOD_RES
<222> LOCATION: (1)..(1)
<223> OTHER INFORMATION: OtBu protection
<220> FEATURE:
<221> NAME/KEY: MOD_RES
<222> LOCATION: (4)..(5)
<223> OTHER INFORMATION: Boc protection
<220> FEATURE:
<221> NAME/KEY: MOD_RES
<222> LOCATION: (12)..(13)
<223> OTHER INFORMATION: tBu protection

<400> SEQUENCE: 10

Gln Phe Val Lys Trp Leu Leu Lys Gly Gly Pro Ser Ser Gly Ala Pro
1               5                   10                  15

Pro Pro Ser Lys
            20
```

```
-continued

<210> SEQ ID NO 11
<211> LENGTH: 19
<212> TYPE: PRT
<213> ORGANISM: Artificial Sequence
<220> FEATURE:
<223> OTHER INFORMATION: Synthetic Peptide (Reference Example 2)
<220> FEATURE:
<221> NAME/KEY: MOD_RES
<222> LOCATION: (1)..(1)
<223> OTHER INFORMATION: OtBu protection
<220> FEATURE:
<221> NAME/KEY: MOD_RES
<222> LOCATION: (4)..(5)
<223> OTHER INFORMATION: Boc protection
<220> FEATURE:
<221> NAME/KEY: MOD_RES
<222> LOCATION: (12)..(13)
<223> OTHER INFORMATION: tBu protection

<400> SEQUENCE: 11

Gln Phe Val Lys Trp Leu Leu Lys Gly Gly Pro Ser Ser Gly Ala Pro
1               5                   10                  15

Pro Pro Ser

<210> SEQ ID NO 12
<211> LENGTH: 23
<212> TYPE: PRT
<213> ORGANISM: Artificial Sequence
<220> FEATURE:
<223> OTHER INFORMATION: Synthetic Peptide (Reference Example 3)
<220> FEATURE:
<221> NAME/KEY: MOD_RES
<222> LOCATION: (2)..(2)
<223> OTHER INFORMATION: Trt protection
<220> FEATURE:
<221> NAME/KEY: MOD_RES
<222> LOCATION: (4)..(4)
<223> OTHER INFORMATION: OtBu protection
<220> FEATURE:
<221> NAME/KEY: MOD_RES
<222> LOCATION: (7)..(8)
<223> OTHER INFORMATION: Boc protection
<220> FEATURE:
<221> NAME/KEY: MOD_RES
<222> LOCATION: (15)..(16)
<223> OTHER INFORMATION: tBu protection

<400> SEQUENCE: 12

Ala Gln Ala Gln Phe Val Lys Trp Leu Leu Lys Gly Gly Pro Ser Ser
1               5                   10                  15

Gly Ala Pro Pro Pro Ser Lys
            20

<210> SEQ ID NO 13
<211> LENGTH: 40
<212> TYPE: PRT
<213> ORGANISM: Artificial Sequence
<220> FEATURE:
<223> OTHER INFORMATION: Synthetic Peptide (Example 1)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
```

<222> LOCATION: (40)..(40)
<223> OTHER INFORMATION: C terminal amidation

<400> SEQUENCE: 13

Tyr Xaa Glu Gly Thr Phe Thr Ser Asp Tyr Ala Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 14
<211> LENGTH: 40
<212> TYPE: PRT
<213> ORGANISM: Artificial Sequence
<220> FEATURE:
<223> OTHER INFORMATION: Synthetic Peptide (Example 2)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 14

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 15
<211> LENGTH: 40
<212> TYPE: PRT
<213> ORGANISM: Artificial Sequence
<220> FEATURE:
<223> OTHER INFORMATION: Synthetic Peptide (Example 3)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 15

```
Tyr Xaa Glu Gly Thr Phe Thr Ser Asp Tyr Ala Ile Xaa Leu Asp Lys
1               5                   10                  15

Gln Ala Gln Ser Glu Phe Val Lys Trp Leu Leu Lys Gly Gly Pro Ser
                20                  25                  30

Ser Gly Ala Pro Pro Pro Ser Lys
        35                  40
```

<210> SEQ ID NO 16
<211> LENGTH: 40
<212> TYPE: PRT
<213> ORGANISM: Artificial Sequence
<220> FEATURE:
<223> OTHER INFORMATION: Synthetic Peptide (Example 4)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 16

```
Tyr Xaa Glu Gly Thr Phe Thr Ser Asp Tyr Xaa Ile Xaa Leu Asp Lys
1               5                   10                  15

Gln Ala Gln Ser Glu Phe Val Lys Trp Leu Leu Lys Gly Gly Pro Ser
                20                  25                  30

Ser Gly Ala Pro Pro Pro Ser Lys
        35                  40
```

<210> SEQ ID NO 17
<211> LENGTH: 39
<212> TYPE: PRT
<213> ORGANISM: Artificial Sequence
<220> FEATURE:
<223> OTHER INFORMATION: Synthetic Peptide (Example 5)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (39)..(39)
<223> OTHER INFORMATION: C terminal amidation

<400> SEQUENCE: 17

```
Tyr Xaa Glu Gly Thr Phe Thr Ser Asp Tyr Ala Ile Xaa Leu Asp Lys
1               5                   10                  15

Gln Ala Gln Ala Glu Phe Val Lys Trp Leu Leu Lys Gly Gly Pro Ser
                20                  25                  30
```

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic Peptide (Example 6)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (39)..(39)
<223> OTHER INFORMATION: C terminal amidation

<400> SEQUENCE: 18

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic Peptide (Example 7)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (39)..(39)
<223> OTHER INFORMATION: C terminal amidation

<400> SEQUENCE: 19

Tyr Xaa Glu Gly Thr Phe Thr Ser Asp Tyr Ala Ile Xaa Leu Asp Lys
1               5                   10                  15

Gln Ala Gln Ser Glu Phe Val Lys Trp Leu Leu Lys Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Synthetic Peptide (Example 8)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (39)..(39)
<223> OTHER INFORMATION: C terminal amidation

<400> SEQUENCE: 20

Tyr Xaa Glu Gly Thr Phe Thr Ser Asp Tyr Xaa Ile Xaa Leu Asp Lys
1               5                   10                  15

Gln Ala Gln Ser Glu Phe Val Lys Trp Leu Leu Lys Gly Gly Pro Ser
            20                  25                  30

Ser Gly Ala Pro Pro Ser
        35

<210> SEQ ID NO 21
<211> LENGTH: 40
<212> TYPE: PRT
<213> ORGANISM: Artificial Sequence
<220> FEATURE:
<223> OTHER INFORMATION: Synthetic Peptide (Example 9)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 21

Tyr Xaa Glu Gly Thr Phe Thr Ser Asp Tyr Xaa Lys Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Ser Lys
        35                  40

<210> SEQ ID NO 22

```
<211> LENGTH: 40
<212> TYPE: PRT
<213> ORGANISM: Artificial Sequence
<220> FEATURE:
<223> OTHER INFORMATION: Synthetic Peptide (Example 10)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 22

Tyr Xaa Glu Gly Thr Phe Thr Ser Asp Tyr Xaa Ala Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 23
<211> LENGTH: 40
<212> TYPE: PRT
<213> ORGANISM: Artificial Sequence
<220> FEATURE:
<223> OTHER INFORMATION: Synthetic Peptide (Example 11)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 23

Tyr Xaa Glu Gly Thr Phe Thr Ser Asp Tyr Xaa Phe Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 24
<211> LENGTH: 40
```

-continued

```
<212> TYPE: PRT
<213> ORGANISM: Artificial Sequence
<220> FEATURE:
<223> OTHER INFORMATION: Synthetic Peptide (Example 12)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (12)..(12)
<223> OTHER INFORMATION: Xaa stands for Pya(4)
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 24

Tyr Xaa Glu Gly Thr Phe Thr Ser Asp Tyr Xaa Xaa Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 25
<211> LENGTH: 40
<212> TYPE: PRT
<213> ORGANISM: Artificial Sequence
<220> FEATURE:
<223> OTHER INFORMATION: Synthetic Peptide (Example 13)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: MOD_RES
<222> LOCATION: (13)..(13)
<223> OTHER INFORMATION: alpha-METHYLATION
<220> FEATURE:
<221> NAME/KEY: MOD_RES
<222> LOCATION: (40)..(40)
<223> OTHER INFORMATION: C terminal amidation

<400> SEQUENCE: 25

Tyr Xaa Glu Gly Thr Phe Thr Ser Asp Tyr Xaa Ile Phe Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40
```

```
<210> SEQ ID NO 26
<211> LENGTH: 40
<212> TYPE: PRT
<213> ORGANISM: Artificial Sequence
<220> FEATURE:
<223> OTHER INFORMATION: Synthetic Peptide (Example 14)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Cha
<220> FEATURE:
<221> NAME/KEY: MOD_RES
<222> LOCATION: (40)..(40)
<223> OTHER INFORMATION: C terminal amidation

<400> SEQUENCE: 26

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 27
<211> LENGTH: 40
<212> TYPE: PRT
<213> ORGANISM: Artificial Sequence
<220> FEATURE:
<223> OTHER INFORMATION: Synthetic Peptide (Example 15)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: MOD_RES
<222> LOCATION: (13)..(13)
<223> OTHER INFORMATION: alpha-METHYLATION
<220> FEATURE:
<221> NAME/KEY: MOD_RES
<222> LOCATION: (40)..(40)
<223> OTHER INFORMATION: C terminal amidation

<400> SEQUENCE: 27

Tyr Xaa Glu Gly Thr Phe Thr Ser Asp Tyr Xaa Lys Phe Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40
```

```
<210> SEQ ID NO 28
<211> LENGTH: 40
<212> TYPE: PRT
<213> ORGANISM: Artificial Sequence
<220> FEATURE:
<223> OTHER INFORMATION: Synthetic Peptide (Example 16)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Cha
<220> FEATURE:
<221> NAME/KEY: MOD_RES
<222> LOCATION: (40)..(40)
<223> OTHER INFORMATION: C terminal amidation

<400> SEQUENCE: 28

Tyr Xaa Glu Gly Thr Phe Thr Ser Asp Tyr Xaa Lys Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Ser Lys
        35                  40

<210> SEQ ID NO 29
<211> LENGTH: 40
<212> TYPE: PRT
<213> ORGANISM: Artificial Sequence
<220> FEATURE:
<223> OTHER INFORMATION: Synthetic Peptide (Example 17)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: MOD_RES
<222> LOCATION: (13)..(13)
<223> OTHER INFORMATION: alpha-METHYLATION
<220> FEATURE:
<221> NAME/KEY: MOD_RES
<222> LOCATION: (40)..(40)
<223> OTHER INFORMATION: C terminal amidation

<400> SEQUENCE: 29

Tyr Xaa Glu Gly Thr Phe Thr Ser Asp Tyr Xaa Ile Tyr Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Ser Lys
        35                  40

<210> SEQ ID NO 30
```

```
<211> LENGTH: 40
<212> TYPE: PRT
<213> ORGANISM: Artificial Sequence
<220> FEATURE:
<223> OTHER INFORMATION: Synthetic Peptide (Example 18)
<220> FEATURE:
<221> NAME/KEY: MOD_RES
<222> LOCATION: (1)..(1)
<223> OTHER INFORMATION: N terminal (acetyl)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 30

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 31
<211> LENGTH: 40
<212> TYPE: PRT
<213> ORGANISM: Artificial Sequence
<220> FEATURE:
<223> OTHER INFORMATION: Synthetic Peptide (Example 19)
<220> FEATURE:
<221> NAME/KEY: MOD_RES
<222> LOCATION: (1)..(1)
<223> OTHER INFORMATION: N terminal (benzoyl)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 31

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
```

```
                   20                  25                  30

Ser Gly Ala Pro Pro Ser Lys
        35                  40

<210> SEQ ID NO 32
<211> LENGTH: 40
<212> TYPE: PRT
<213> ORGANISM: Artificial Sequence
<220> FEATURE:
<223> OTHER INFORMATION: Synthetic Peptide (Example 20)
<220> FEATURE:
<221> NAME/KEY: MOD_RES
<222> LOCATION: (1)..(1)
<223> OTHER INFORMATION: N terminal (4-PyCO (4-pyridylcarbonyl))
<220> FEATURE:
<221> NAME/KEY: MOD_RES
<222> LOCATION: (1)..(1)
<223> OTHER INFORMATION: N terminal (4-PyCO (4-pyridylcarbonyl))
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 32

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Ser Lys
        35                  40

<210> SEQ ID NO 33
<211> LENGTH: 40
<212> TYPE: PRT
<213> ORGANISM: Artificial Sequence
<220> FEATURE:
<223> OTHER INFORMATION: Synthetic Peptide (Example 21)
<220> FEATURE:
<221> NAME/KEY: MOD_RES
<222> LOCATION: (1)..(1)
<223> OTHER INFORMATION: N terminal (cPrCO (Cyclopropanecarbonyl))
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
```

```
<220> FEATURE:
<221> NAME/KEY: MOD_RES
<222> LOCATION: (40)..(40)
<223> OTHER INFORMATION: C terminal amidation

<400> SEQUENCE: 33

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 34
<211> LENGTH: 40
<212> TYPE: PRT
<213> ORGANISM: Artificial Sequence
<220> FEATURE:
<223> OTHER INFORMATION: Synthetic Peptide (Example 22)
<220> FEATURE:
<221> NAME/KEY: MOD_RES
<222> LOCATION: (1)..(1)
<223> OTHER INFORMATION: N terminal (amidino)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 34

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 35
<211> LENGTH: 40
<212> TYPE: PRT
<213> ORGANISM: Artificial Sequence
<220> FEATURE:
<223> OTHER INFORMATION: Synthetic Peptide (Example 23)
<220> FEATURE:
<221> NAME/KEY: MOD_RES
<222> LOCATION: (1)..(1)
<223> OTHER INFORMATION: N-METHYLATION
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
```

<221> NAME/KEY: misc_feature
<222> LOCATION: (11)..(11)
<223> OTHER INFORMATION: Xaa stands for Aib
<220> FEATURE:
<221> NAME/KEY: misc_feature
<222> LOCATION: (13)..(13)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 35

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 36
<211> LENGTH: 40
<212> TYPE: PRT
<213> ORGANISM: Artificial Sequence
<220> FEATURE:
<223> OTHER INFORMATION: Synthetic Peptide (Example 24)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 36

Tyr Xaa Glu Gly Thr Phe Thr Ser Asp Tyr Xaa Lys Tyr Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 37
<211> LENGTH: 40
<212> TYPE: PRT
<213> ORGANISM: Artificial Sequence
<220> FEATURE:
<223> OTHER INFORMATION: Synthetic Peptide (Example 25)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: MOD_RES
<222> LOCATION: (40)..(40)
<223> OTHER INFORMATION: C terminal amidation

<400> SEQUENCE: 37

Tyr Xaa Glu Gly Thr Phe Thr Ser Asp Tyr Xaa Lys Tyr Leu Asp Lys
1               5                   10                  15

Gln Ala Gln Gln Glu Phe Val Lys Trp Leu Leu Lys Gly Gly Pro Ser
            20                  25                  30

Ser Gly Ala Pro Pro Pro Ser Lys
        35                  40

<210> SEQ ID NO 38
<211> LENGTH: 39
<212> TYPE: PRT
<213> ORGANISM: Artificial Sequence
<220> FEATURE:
<223> OTHER INFORMATION: Synthetic Peptide (Example 26)
<220> FEATURE:
<221> NAME/KEY: misc_feature
<222> LOCATION: (2)..(2)
<223> OTHER INFORMATION: Xaa stands for Aib
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: misc_feature
<222> LOCATION: (11)..(11)
<223> OTHER INFORMATION: Xaa stands for Aib
<220> FEATURE:
<221> NAME/KEY: MOD_RES
<222> LOCATION: (39)..(39)
<223> OTHER INFORMATION: C terminal amidation

<400> SEQUENCE: 38

Tyr Xaa Glu Gly Thr Phe Thr Ser Asp Tyr Xaa Lys Tyr Leu Asp Lys
1               5                   10                  15

Gln Ala Gln Gln Glu Phe Val Lys Trp Leu Leu Lys Gly Gly Pro Ser
            20                  25                  30

Ser Gly Ala Pro Pro Pro Ser
        35

<210> SEQ ID NO 39
<211> LENGTH: 40
<212> TYPE: PRT
<213> ORGANISM: Artificial Sequence
<220> FEATURE:
<223> OTHER INFORMATION: Synthetic Peptide (Example 1)
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)

```
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 39

Tyr Xaa Glu Gly Thr Phe Thr Ser Asp Tyr Ala Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 40
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
```

```
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
```

<222> LOCATION: (40)..(40)
<223> OTHER INFORMATION: Boc protection

<400> SEQUENCE: 40

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Ser Lys
        35              40

<210> SEQ ID NO 41
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES

```
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 41

Tyr Xaa Glu Gly Thr Phe Thr Ser Asp Tyr Ala Ile Xaa Leu Asp Lys
1               5                   10                  15

Gln Ala Gln Ser Glu Phe Val Lys Trp Leu Leu Lys Gly Gly Pro Ser
            20                  25                  30

Ser Gly Ala Pro Pro Pro Ser Lys
        35                  40

<210> SEQ ID NO 42
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
```

```
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (20)..(20)
<223> OTHER INFORMATION: tBu protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 42

Tyr Xaa Glu Gly Thr Phe Thr Ser Asp Tyr Xaa Ile Xaa Leu Asp Lys
1               5                   10                  15

Gln Ala Gln Ser Glu Phe Val Lys Trp Leu Leu Lys Gly Gly Pro Ser
            20                  25                  30

Ser Gly Ala Pro Pro Pro Ser Lys
        35                  40

<210> SEQ ID NO 43
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
```

<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: C terminal amidation
<220> FEATURE:
<221> NAME/KEY: MOD_RES
<222> LOCATION: (39)..(39)
<223> OTHER INFORMATION: tBu protection

<400> SEQUENCE: 43

Tyr Xaa Glu Gly Thr Phe Thr Ser Asp Tyr Ala Ile Xaa Leu Asp Lys
1               5                   10                  15

Gln Ala Gln Ala Glu Phe Val Lys Trp Leu Leu Lys Gly Gly Pro Ser
                20                  25                  30

Ser Gly Ala Pro Pro Pro Ser
            35

```
<210> SEQ ID NO 44
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
```

<221> NAME/KEY: MOD_RES
<222> LOCATION: (39)..(39)
<223> OTHER INFORMATION: C terminal amidation
<220> FEATURE:
<221> NAME/KEY: MOD_RES
<222> LOCATION: (39)..(39)
<223> OTHER INFORMATION: tBu protection

<400> SEQUENCE: 44

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:

-continued

```
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: C terminal amidation
<220> FEATURE:
<221> NAME/KEY: MOD_RES
<222> LOCATION: (39)..(39)
<223> OTHER INFORMATION: tBu protection

<400> SEQUENCE: 45

Tyr Xaa Glu Gly Thr Phe Thr Ser Asp Tyr Ala Ile Xaa Leu Asp Lys
 1               5                   10                  15

Gln Ala Gln Ser Glu Phe Val Lys Trp Leu Leu Lys Gly Gly Pro Ser
            20                  25                  30

Ser Gly Ala Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
```

<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (20)..(20)
<223> OTHER INFORMATION: tBu protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: C terminal amidation
<220> FEATURE:
<221> NAME/KEY: MOD_RES
<222> LOCATION: (39)..(39)
<223> OTHER INFORMATION: tBu protection

<400> SEQUENCE: 46

Tyr Xaa Glu Gly Thr Phe Thr Ser Asp Tyr Xaa Ile Xaa Leu Asp Lys
1               5                   10                  15
Gln Ala Gln Ser Glu Phe Val Lys Trp Leu Leu Lys Gly Gly Pro Ser
            20                  25                  30
Ser Gly Ala Pro Pro Ser
        35

<210> SEQ ID NO 47
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:

```
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MOD_RES
<222> LOCATION: (12)..(12)
<223> OTHER INFORMATION: Boc protection
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 47

Tyr Xaa Glu Gly Thr Phe Thr Ser Asp Tyr Xaa Lys Xaa Leu Asp Lys
```

```
1               5                   10                  15
Gln Ala Gln Ala Glu Phe Val Lys Trp Leu Leu Lys Gly Gly Pro Ser
                20                  25                  30
Ser Gly Ala Pro Pro Ser Lys
        35                  40

<210> SEQ ID NO 48
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
```

```
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 48

Tyr Xaa Glu Gly Thr Phe Thr Ser Asp Tyr Xaa Ala Xaa Leu Asp Lys
 1               5                  10                  15

Gln Ala Gln Ala Glu Phe Val Lys Trp Leu Leu Lys Gly Gly Pro Ser
             20                  25                  30

Ser Gly Ala Pro Pro Pro Ser Lys
         35                  40

<210> SEQ ID NO 49
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
```

```
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 49

Tyr Xaa Glu Gly Thr Phe Thr Ser Asp Tyr Xaa Phe Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Ser Lys
        35                  40

<210> SEQ ID NO 50
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
```

```
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (12)..(12)
<223> OTHER INFORMATION: Xaa stands for Pya(4)
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 50

Tyr Xaa Glu Gly Thr Phe Thr Ser Asp Tyr Xaa Xaa Xaa Leu Asp Lys
1               5                   10                  15

Gln Ala Gln Ala Glu Phe Val Lys Trp Leu Leu Lys Gly Gly Pro Ser
```

```
                20                  25                  30

Ser Gly Ala Pro Pro Pro Ser Lys
        35                  40

<210> SEQ ID NO 51
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MOD_RES
<222> LOCATION: (13)..(13)
<223> OTHER INFORMATION: alpha-METHYLATION
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
```

<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 51

Tyr Xaa Glu Gly Thr Phe Thr Ser Asp Tyr Xaa Ile Phe Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 52
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Cha
<220> FEATURE:
<221> NAME/KEY: MOD_RES
<222> LOCATION: (15)..(15)

```
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 52

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 53
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
```

```
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MOD_RES
<222> LOCATION: (12)..(12)
<223> OTHER INFORMATION: Boc protection
<220> FEATURE:
<221> NAME/KEY: MOD_RES
<222> LOCATION: (13)..(13)
<223> OTHER INFORMATION: alpha-METHYLATION
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 53

Tyr Xaa Glu Gly Thr Phe Thr Ser Asp Tyr Xaa Lys Phe Leu Asp Lys
 1               5                  10                  15

Gln Ala Gln Ala Glu Phe Val Lys Trp Leu Leu Lys Gly Gly Pro Ser
            20                  25                  30

Ser Gly Ala Pro Pro Pro Ser Lys
```

<210> SEQ ID NO 54
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MOD_RES
<222> LOCATION: (12)..(12)
<223> OTHER INFORMATION: Boc protection
<220> FEATURE:
<221> NAME/KEY: MISC_FEATURE
<222> LOCATION: (13)..(13)
<223> OTHER INFORMATION: Xaa stands for Cha
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 54

Tyr Xaa Glu Gly Thr Phe Thr Ser Asp Tyr Xaa Lys Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Ser Lys
        35                  40

<210> SEQ ID NO 55
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MOD_RES
<222> LOCATION: (13)..(13)
<223> OTHER INFORMATION: alpha-METHYLATION
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 55

Tyr Xaa Glu Gly Thr Phe Thr Ser Asp Tyr Xaa Ile Tyr Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 56
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N terminal (acetyl)
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES

```
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 56

Tyr Xaa Glu Gly Thr Phe Thr Ser Asp Tyr Xaa Ile Xaa Leu Asp Lys
 1               5                  10                  15

Gln Ala Gln Ala Glu Phe Val Lys Trp Leu Leu Lys Gly Gly Pro Ser
             20                  25                  30
```

Ser Gly Ala Pro Pro Pro Ser Lys
            35                  40

<210> SEQ ID NO 57
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N terminal (benzoyl)
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:

```
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 57

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 58
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N terminal (4-PyCO(4-pyridylcarbonyl))
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
```

```
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 58

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 59
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N terminal (cPrCO(Cyclopropanecarbonyl))
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
```

```
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 59

Tyr Xaa Glu Gly Thr Phe Thr Ser Asp Tyr Xaa Ile Xaa Leu Asp Lys
```

```
1               5                   10                  15
Gln Ala Gln Ala Glu Phe Val Lys Trp Leu Leu Lys Gly Gly Pro Ser
                20                  25                  30
Ser Gly Ala Pro Pro Ser Lys
        35              40

<210> SEQ ID NO 60
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N terminal (amidino)
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
```

```
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 60

Tyr Xaa Glu Gly Thr Phe Thr Ser Asp Tyr Xaa Ile Xaa Leu Asp Lys
1               5                   10                  15

Gln Ala Gln Ala Glu Phe Val Lys Trp Leu Leu Lys Gly Gly Pro Ser
                20                  25                  30

Ser Gly Ala Pro Pro Pro Ser Lys
            35                  40

<210> SEQ ID NO 61
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: N-METHYLATION
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
```

```
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MISC_FEATURE
<222> LOCATION: (13)..(13)
<223> OTHER INFORMATION: Xaa stands for Aib
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 61

Tyr Xaa Glu Gly Thr Phe Thr Ser Asp Tyr Xaa Ile Xaa Leu Asp Lys
 1               5                  10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 62
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
```

-continued

```
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MOD_RES
<222> LOCATION: (12)..(12)
<223> OTHER INFORMATION: Boc protection
<220> FEATURE:
<221> NAME/KEY: MOD_RES
<222> LOCATION: (13)..(13)
<223> OTHER INFORMATION: tBu protection
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
```

<223> OTHER INFORMATION: Boc protection

<400> SEQUENCE: 62

Tyr Xaa Glu Gly Thr Phe Thr Ser Asp Tyr Xaa Lys Tyr Leu Asp Lys
1               5                   10                  15

Gln Ala Gln Ala Glu Phe Val Lys Trp Leu Leu Lys Gly Gly Pro Ser
            20                  25                  30

Ser Gly Ala Pro Pro Pro Ser Lys
        35                  40

<210> SEQ ID NO 63
<211> LENGTH: 40
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MOD_RES
<222> LOCATION: (12)..(12)
<223> OTHER INFORMATION: Boc protection
<220> FEATURE:
<221> NAME/KEY: MOD_RES
<222> LOCATION: (13)..(13)
<223> OTHER INFORMATION: tBu protection
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)

```
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: tBu protection
<220> FEATURE:
<221> NAME/KEY: MOD_RES
<222> LOCATION: (40)..(40)
<223> OTHER INFORMATION: C terminal amidation
<220> FEATURE:
<221> NAME/KEY: MOD_RES
<222> LOCATION: (40)..(40)
<223> OTHER INFORMATION: Boc protection

<400> SEQUENCE: 63

Tyr Xaa Glu Gly Thr Phe Thr Ser Asp Tyr Xaa Lys Tyr Leu Asp Lys
1               5                   10                  15

Gln Ala Gln Gln Glu Phe Val Lys Trp Leu Leu Lys Gly Gly Pro Ser
            20                  25                  30

Ser Gly Ala Pro Pro Pro Ser Lys
        35                  40

<210> SEQ ID NO 64
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: tBu protection
<220> FEATURE:
<221> NAME/KEY: MISC_FEATURE
<222> LOCATION: (2)..(2)
<223> OTHER INFORMATION: Xaa stands for Aib
<220> FEATURE:
<221> NAME/KEY: MOD_RES
<222> LOCATION: (3)..(3)
<223> OTHER INFORMATION: OtBu protection
<220> FEATURE:
<221> NAME/KEY: MOD_RES
<222> LOCATION: (5)..(5)
<223> OTHER INFORMATION: tBu protection
<220> FEATURE:
<221> NAME/KEY: MOD_RES
<222> LOCATION: (6)..(6)
<223> OTHER INFORMATION: alpha-METHYLATION
<220> FEATURE:
<221> NAME/KEY: MOD_RES
<222> LOCATION: (7)..(8)
<223> OTHER INFORMATION: tBu protection
<220> FEATURE:
<221> NAME/KEY: MOD_RES
<222> LOCATION: (9)..(9)
<223> OTHER INFORMATION: OtBu protection
<220> FEATURE:
<221> NAME/KEY: MOD_RES
<222> LOCATION: (10)..(10)
```

```
<223> OTHER INFORMATION: tBu protection
<220> FEATURE:
<221> NAME/KEY: MISC_FEATURE
<222> LOCATION: (11)..(11)
<223> OTHER INFORMATION: Xaa stands for Aib
<220> FEATURE:
<221> NAME/KEY: MOD_RES
<222> LOCATION: (12)..(12)
<223> OTHER INFORMATION: Boc protection
<220> FEATURE:
<221> NAME/KEY: MOD_RES
<222> LOCATION: (13)..(13)
<223> OTHER INFORMATION: tBu protection
<220> FEATURE:
<221> NAME/KEY: MOD_RES
<222> LOCATION: (15)..(15)
<223> OTHER INFORMATION: OtBu protection
<220> FEATURE:
<221> NAME/KEY: MOD_RES
<222> LOCATION: (16)..(16)
<223> OTHER INFORMATION: Boc protection
<220> FEATURE:
<221> NAME/KEY: MOD_RES
<222> LOCATION: (17)..(17)
<223> OTHER INFORMATION: Trt protection
<220> FEATURE:
<221> NAME/KEY: MOD_RES
<222> LOCATION: (19)..(19)
<223> OTHER INFORMATION: Trt protection
<220> FEATURE:
<221> NAME/KEY: MOD_RES
<222> LOCATION: (20)..(20)
<223> OTHER INFORMATION: Trt protection
<220> FEATURE:
<221> NAME/KEY: MOD_RES
<222> LOCATION: (21)..(21)
<223> OTHER INFORMATION: OtBu protection
<220> FEATURE:
<221> NAME/KEY: MOD_RES
<222> LOCATION: (24)..(25)
<223> OTHER INFORMATION: Boc protection
<220> FEATURE:
<221> NAME/KEY: MOD_RES
<222> LOCATION: (28)..(28)
<223> OTHER INFORMATION: Boc protection
<220> FEATURE:
<221> NAME/KEY: MOD_RES
<222> LOCATION: (32)..(33)
<223> OTHER INFORMATION: tBu protection
<220> FEATURE:
<221> NAME/KEY: MOD_RES
<222> LOCATION: (39)..(39)
<223> OTHER INFORMATION: C terminal amidation
<220> FEATURE:
<221> NAME/KEY: MOD_RES
<222> LOCATION: (39)..(39)
<223> OTHER INFORMATION: tBu protection

<400> SEQUENCE: 64

Tyr Xaa Glu Gly Thr Phe Thr Ser Asp Tyr Xaa Lys Tyr Leu Asp Lys
1               5                   10                  15

Gln Ala Gln Gln Glu Phe Val Lys Trp Leu Leu Lys Gly Gly Pro Ser
                20                  25                  30

Ser Gly Ala Pro Pro Pro Ser
            35
```